(12) United States Patent
Huang

(10) Patent No.: US 9,938,274 B1
(45) Date of Patent: Apr. 10, 2018

(54) NAPHTHYRIDINE COMPOUNDS, MEDICAL COMBINATIONS AND USE THEREOF

(71) Applicants: Nanjing Natinefy Pharmatech Co., Ltd., Nanjing (CN); WUHAN NOVAFFEY SCIENCE & TECHNOLOGY CO., LTD., Wuhan (CN)

(72) Inventor: Wei Huang, Wuhan (CN)

(73) Assignees: NANJING NATINEFY PHARMATECH CO., LTD., Nanjing (CN); WUHAN NOVAFFEY SCIENCE & TECHNOLOGY CO., LTD., Wuhan (CN)

( * ) Notice: Subject to any disclaimer, the term of this patent is extended or adjusted under 35 U.S.C. 154(b) by 0 days.

(21) Appl. No.: 15/402,768

(22) Filed: Jan. 10, 2017

(30) Foreign Application Priority Data

Oct. 9, 2016 (CN) .......................... 2016 1 0880102

(51) Int. Cl.
*C07D 471/04* (2006.01)

(52) U.S. Cl.
CPC .................. *C07D 471/04* (2013.01)

(58) Field of Classification Search
CPC .................................................... C07D 471/04
See application file for complete search history.

(56) References Cited

FOREIGN PATENT DOCUMENTS

WO 2013/097753 * 7/2013

* cited by examiner

Primary Examiner — D Margaret M Seaman
(74) Attorney, Agent, or Firm — Volpe and Koenig, P.C.

(57) ABSTRACT

This invention involves the field of biomedicine, and reveals naphthyridine compounds, medical combinations and use thereof. The naphthyridine compounds has the structure as shown by Formula (I), or its stereoisomers, geometric isomers, tautomers, nitrogen oxides, hydrates, solvates, metabolites, pharmaceutically acceptable salts or their prodrugs. The naphthyridine compounds of this invention has anti-tumor efficacy significantly superior to that of prior art. Moreover, the naphthyridine compounds of this invention can treat diseases mediated by protein kinases.

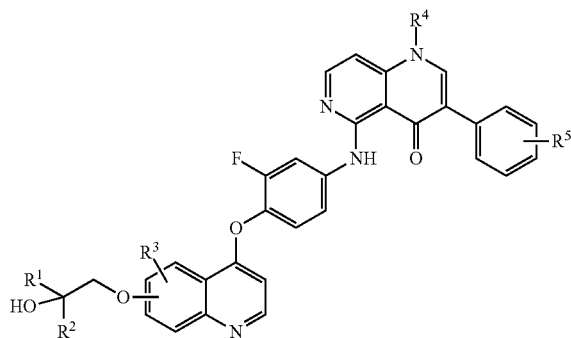

(I)

5 Claims, 1 Drawing Sheet

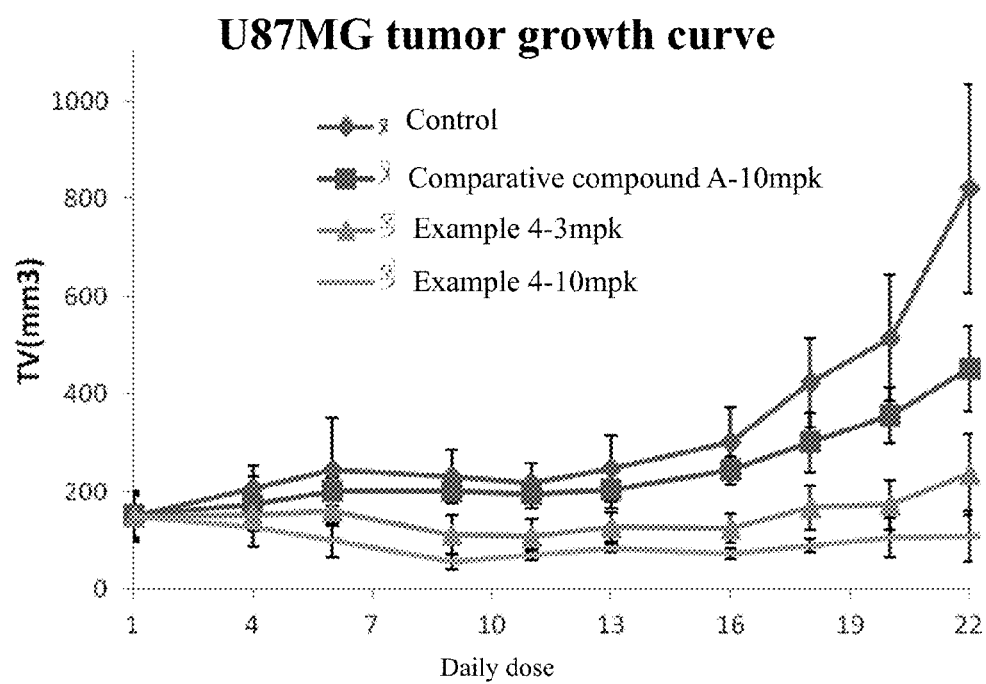

NAPHTHYRIDINE COMPOUNDS, MEDICAL COMBINATIONS AND USE THEREOF

CROSS REFERENCE TO RELATED APPLICATION

This application claims priority to Chinese Patent Application No. 201610880102.6, filed Oct. 9, 2016, which is incorporated herein by reference as if fully set forth.

FIELD OF THE INVENTION

This invention involves the field of biomedicine, specifically naphthyridine compounds. This invention also involves use of these naphthyridine compounds as protein kinase inhibitors.

BACKGROUND

Protein kinases are the largest gene family in eucaryotic cells. They play essential regulating roles in multiple cellular processes, such as: cell proliferation, cell death, cell cycle process, differentiation, cell survival, etc. Protein Tyrosine Kinases (PTKs) are the most important category among the protein kinase family. PTKs play an important part in the signal transduction mechanism of normal cells. Their abnormal expression may cause many diseases, especially tumorigenesis, therefore, inhibiting overexpression of tyrosine kinases to restore physiological balance will become a new therapeutic regimen.

In the last 10 years, several innovative antitumor drugs based on signal pathway of tyrosine kinases have been successfully developed. Moreover, tyrosine kinases inhibitors (TKIs) has characteristics such as small molecules, orally effective and good tolerance, thus have been approved for treating multiple tumors, such as: lung cancer, breast cancer, renal carcinoma, pancreatic cancer, gastrointestinal cancer, chronic leukemia, etc.

More and more basic research and clinical studies demonstrate: tumor is a disease affected by multiple factors and signals, and its pathogenesis is very complicated (Giamas G., Man Y. L., Hirner H. Bischof J, Kramer K, Khan K, Ahmed S S, Stebbing J, Knippschild U. Kinases as targets in the treatment of solid tumors. Cell Signal 2010, 22(7), 984-1002). Multi-kinase inhibitors may inhibit or block several transducing pathways of cell growth signals, therefore, have already been the focus of tumor treatment and new medicine development.

c-Met is an important member of the tyrosine kinase family, which belongs to a receptor tyrosine kinases (RTK). c-Met was initially considered as an oncogenic fusion protein (TPR-MET), however, it has now been demonstrated that c-Met is a tyrosine kinases receptor coded by the proto-oncogene MET. It is the only high-affinity receptor of hepatocyte growth factor (HGF). During tumor onset and development, especially those with invasion and metastasis potential, HGF/c-Met signal pathway play an essential role. Tumor cells may stimulate adjacent fibroblasts to secrete HGF through releasing cytokines such as IL-1, FGF-2, and PDGF. Some tumor cells may show overexpression of both c-Met and HGF through autocrine route. Overexpression of c-Met may be observed in human hepatoma, cholangiocarcinoma, pancreatic cancer, lung cancer, thyroid cancer, pleural interstitialoma, etc. In case of metastatic tumor, HGF/c-Met signal pathway may influence tumor cell adhesion, promote degradation of extracellular matrix, induce angiogenesis, and facilitate cellular proliferation. Using the HGF/c-Met signal pathway as the target, it is relatively easy to realize simultaneous interference of multiple pathways. Once the HGF/c-Met signal pathway that shows abnormal activation and overexpression has been blocked in tumor cells, tumor cells will exert a series of changes including altered cell morphology, slower proliferation, lower tumorigenicity, and decreased invasion ability. (The MET oncogene drives a genetic programme linking cancer to haemostasis. *Nature* 2005, 434, 396-400; Drug development of MET inhibitors: targeting oncogene addiction and expedience. *Nat. Rev. Drug Discov.* 2008, 7, 504-516; Targeting receptor tyrosine kinase MET in cancer: small molecule inhibitors and clinical progress. *J. Med. Chem.* 2014, 57, 4427-4453.)

Vascular endothelial growth factor (VEGF) is the most effective and specific one among all pro-angiogenic factors which have been found up to now. VEGF may regulate process such as vascular geneisis, angiopoiesis and vascular migration, shows overexpression in many malignant tumors, and is closely related to growth, metastasis and prognosis. VEGFRs are tyrosine kinase transmembrane glycoproteins. VEGFR mainly include 3 receptors, VEGFR-1 (Flt-1), VEGFR-2 (KDR/Flk-1), and VEGFR-3 (Flt-4). VEGFR-2 is a specific glycoprotein, and has a relative molecular weight of 210000-230000. It mainly exists in vascular endothelial cells and hemopoietic stem cells. It may bind with VEGF-A, VEGF-C, VEGF-D, and VEGF-E, and mainly regulate the physiological reaction of VEGF in vascular endothelial cells, including permeability, proliferation and migration, therefore, it is a key signal transducer in physiological and pathologic angiogenic processes. VEGFR-2 exerts overexpression in case of ovarian cancer, thyroid cancer, melanoma and medulloblastoma, and supplies vast majorities of tumor tissues with nutrient by regulating tumor vascular system (including blood and lymph fluid). Additionally, the expression level of VEGFR-2 in tumors such as malignant intestinal cancer, lung cancer, and breast cancer is also significantly higher than that in non-tumor tissue. Some medicine may target at VEGFR signal response. Whether given alone or in combination with other chemotherapies, they are effective for patients with advanced malignant tumor. (An overview of small molecule inhibitors of VEGFR signaling. *Nat. Rev. Clin. Oncol.* 2009, 6, 569-579; Principles and mechanisms of vessel normalization for cancer and other angiogenic diseases. *Nat. Rev. Drug Discovery* 2011, 10, 417-427; Vascular Endothelial Growth Factor (VEGF) Receptors: Drugs and New Inhibitors. *J. Med. Chem.* 2012, 55, 10797-10822).

Axl kinase is a member of the TAM receptor tyrosine kinase family, binding with ligand Gas6 may activate Axl, thus initiate its downstream signal transducing pathway, and play a part in processes such as cell growth, migration, aggregation and apoptosis. A recent study shows, Axl kinase exerts overexpression or activation in many cancers, especially in cancer cells that develop resistance after chemotherapy and receptor tyrosine kinase inhibitor (TKI), the overexpression of Axl is very significant, and this is an important cause of developing resistance. Therefore, Axl kinase inhibitor is a new regimen to treat cancer. (Axl Kinase as a Key Target for Oncology: Focus on Small Molecule Inhibitors. *Mol. Cancer Ther.* 2014, 13, 2141-2148).

RET is a receptor tyrosine kinase, as a cell surface molecule, it can convert the signal for cell growth and differentiation. RET plays an important role in the development of nervous crest. Moreover, due to the rearrangement of cytogenetics, the carcinogenicity may be activated both in vivo and in vitro. The mutation caused by RET gene is related to multiple endocrine neoplasia, congenital megacolon, and medullary carcinoma of thyroid. The mutation with enhanced RET function may cause: medullary carcinoma of thyroid, onset of multiple endocrine neoplasia (types 2A and 2B), chromaffinoma, and parathyroid hyperplasia. RET rearrangement also occurs frequently in non-small cell lung cancer, and is closely related to onset and development of lung cancer. (Development of RET kinase inhibitors for targeted cancer therapy. Curr. Med. Chem. 2011, 18, 162-175).

Other pathogenic conditions related to protein kinases include psoriasis, liver cirrhosis, diabetes mellitus, angiogenesis, restenosis, ophthalmic diseases, rheumatoid arthritis and other inflammatory diseases, immunologically mediated disease, cardiovascular diseases such as arteriosclerosis, and many renal diseases.

Naphthyridine derivatives have broad-spectrum bioactivities, and important applications in the pharmaceutical field. In last years, many small molecules bearing naphthyridine scaffold have been widely used as protein kinase inhibitor in treating many diseases related to abnormal kinase activity, such as tumor, psoriasis, liver cirrhosis, diabetes mellitus, angiogenesis, ophthalmic diseases, rheumatoid arthritis and other inflammatory diseases, immunologically mediated disease, cardiovascular diseases such as arteriosclerosis, and many renal diseases. Wherein, 2,7-naphthyridines (WO2013033981, WO0192256, WO0242264), 1,5-naphthyridines (WO2006106046), 1,6-naphthyridines (WO2007060028, WO2010037249, WO2010088177), 2,6-naphthyridines (WO2008122614), fused heterocyclic naphthyridines (WO2009148887, WO2009148916), 2,7-naphthyridinones (WO2008109613, WO2009097287, WO2013033981), and 1,8-naphthyridinones (WO2010002779) are also used as protein kinase inhibitor.

1,6-naphthyridines-1(2H)-ketones are important naphthyridine compounds, with a molecular formula of $C_8H_6N_2O$, and a molecular weight of 146.1, and they have the chemical structure as shown above.

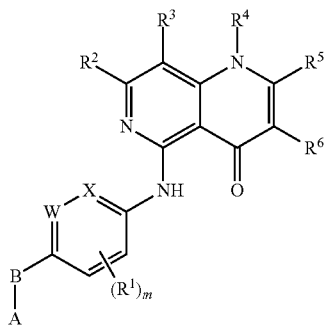

General Formula of Compounds Revealed by WO2013097753

1,6-naphthyridines-1(2H)-ketones have been rarely reported to be used as therapeutic protein kinase inhibitor, and only the patent WO2013097753 revealed a category of 1,6-naphthyridines-1(2H)-ketones as c-Met kinase inhibitor. This patent focuses on a series of compounds whose block A is replaced by quinazoline. However, analyzing the structural characteristics of some commercial kinase inhibitors shows, when the block A is a quinoline ring, the pharmaceutical potential of the compounds is higher. Therefore, this invention attempts to develop naphthyridines with more structural types, and better kinase inhibiting activity and efficacy against diseases.

SUMMARY

In an aspect, the invention relates to a naphthyridine compound as shown by Formula (I), or its stereoisomers, geometric isomers, tautomers, nitrogen oxides, hydrates, solvates, metabolites, pharmaceutically acceptable salts or their prodrugs:

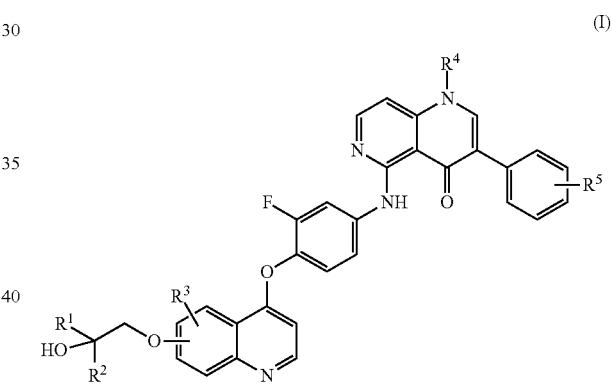

(I)

$R^1$ and $R^2$ are chosen from H and $C_1$-$C_3$ alkyl. $R^3$ is chosen from H and $C_1$-$C_3$ alkoxyl. $R^4$ is chosen from H, $C_1$-$C_6$ alkyl, full-carbon mono-cycloalkyl with 3 to 8 members, heteroalicyclic group with 3 to 8 members, wherein the $C_1$-$C_6$ alkyl, the full-carbon mono-cycloalkyl with 3 to 8 members, and the heteroalicyclic group with 3 to 8 members are optionally further substituted by one or more substituent(s) selected from $C_1$-$C_6$ alkyl, $C_1$-$C_6$ alkoxyl, heteroalicyclic group with 3 to 8 members, $C_6$-$C_{10}$ aryl, $C_5$-$C_{10}$ heteroaryl or hydroxyl. $R^5$ is chosen from H, F, Cl, Br, I, CN, $C_{1-3}$ alkyl, or $C_{1-3}$ haloalkyl.

In an aspect the invention relates to a method of preparing a medicine. The method comprises providing a naphthyridine compound as shown by Formula (I), or its stereoisomers, geometric isomers, tautomers, nitrogen oxides, hydrates, solvates, metabolites, pharmaceutically acceptable salts or their prodrugs:

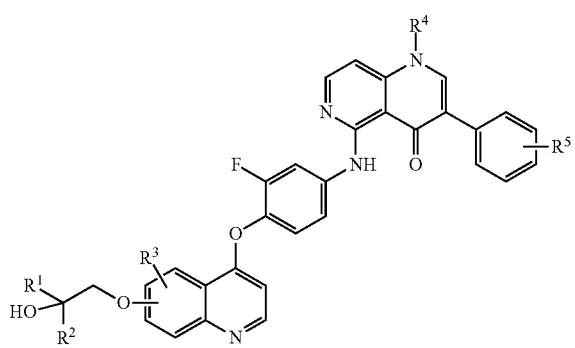

(I)

$R^1$ and $R^2$ are chosen from H and $C_1$-$C_3$ alkyl. $R^3$ is chosen from H and $C_1$-$C_3$ alkoxyl. $R^4$ is chosen from H, $C_1$-$C_6$ alkyl, full-carbon mono-cycloalkyl with 3 to 8 members, heteroalicyclic group with 3 to 8 members, wherein the $C_1$-$C_6$ alkyl, the full-carbon mono-cycloalkyl with 3 to 8 members, and the heteroalicyclic group with 3 to 8 members are optionally further substituted by one or more substituent(s) selected from $C_1$-$C_6$ alkyl, $C_1$-$C_6$ alkoxyl, heteroalicyclic group with 3 to 8 members, $C_6$-$C_{10}$ aryl, $C_5$-$C_{10}$ heteroaryl or hydroxyl. $R^5$ is chosen from H, F, Cl, Br, I, CN, $C_{1-3}$ alkyl, or $C_{1-3}$ haloalkyl. The

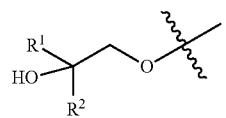

and $R^3$ may be located at 6- and 7- of the quinolyl ring, or 7- and 6- of the quinolyl ring, respectively. $R^1$ and $R^2$ may be chosen from H and $C_1$-$C_3$ alkyl, but where $R^1$ and $R^2$ are not hydrogen simultaneously. $R^4$ may be chosen from H, $C_1$-$C_6$ alkyl, full-carbon mono-cycloalkyl with 3 to 8 members, $C_1$-$C_6$ alkylidene substituted by heteroalicyclic group with 3 to 8 members, $C_1$-$C_6$ alkoxyl-$C_1$-$C_6$ alkylidene, or $C_6$-$C_{10}$ aryl-$C_1$-$C_6$ alkylidene. $R^4$ may be chosen from hydrogen, methyl, ethyl, propyl, isopropyl, cyclopropyl,

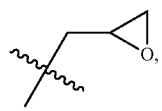

2-methoxyethyl, 2-hydroxyethyl or benzyl. The naphthyridine compound may have one of structures (1) to (18), or the structure of their stereoisomers, geometric isomers, tautomers, nitrogen oxides, hydrates, solvates, metabolites, pharmaceutically acceptable salts or their prodrugs.

BRIEF DESCRIPTION OF THE DRAWINGS

Figures are intended for helping further understanding of this invention, and as part of the description, they will be used to explain this invention together with the specific embodiments as following, but are not intended to impose any limit on this invention. Among the figures:

FIG. 1 is the U87MG tumor growth curve of Example 4 and comparative compound A.

DETAILED DESCRIPTION

This invention aims at providing a new type of naphthyridine compounds, which are intended for treating all tumors.

Through many scientific studies, the inventor prepared naphthyridine compounds with the structure as shown in Formula (I), and found that naphthyridine compounds exerts excellent inhibiting activity on c-Met and VEGFR-2, which is significantly better than that of typical compounds A and B revealed by patent WO2013097753. More importantly, the in vivo anti-tumor activity of these naphthyridine compounds is also significantly superior to that of typical compound A, therefore, they demonstrate better efficacy against tumor.

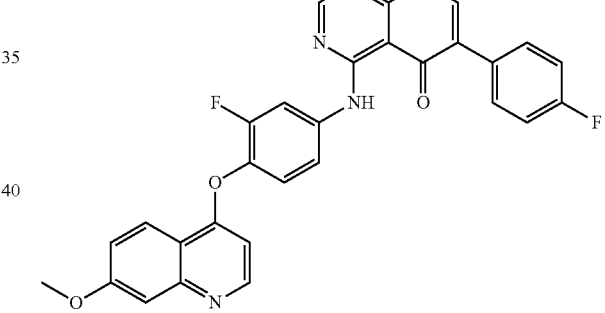

Typical compound A/Example 7
(WO2013097753)

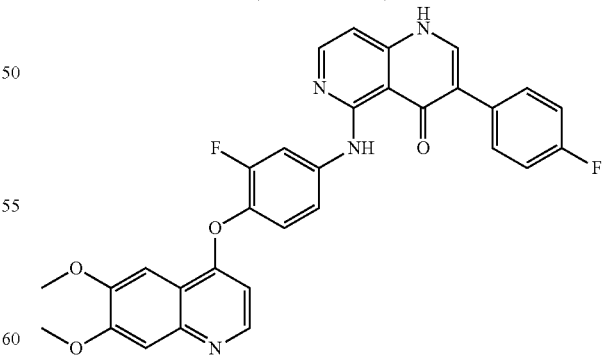

Typical compound A/Example 19
(WO2013097753)

This invention involves compounds as shown by Formula (I):

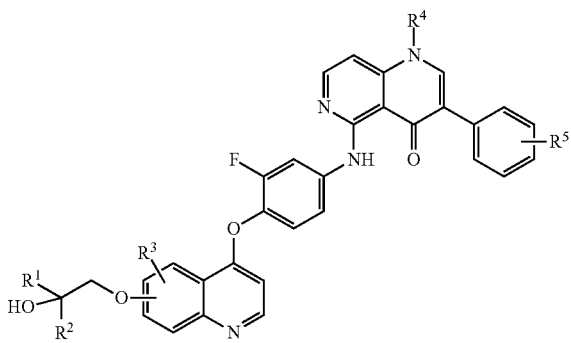

(I)

or their stereoisomers, geometric isomers, tautomers, nitrogen oxides, hydrates, solvates, metabolites, pharmaceutically acceptable salts or their prodrugs, wherein:

$R^1$ and $R^2$ are chosen from H and $C_1$-$C_3$ alkyl;

$R^3$ is chosen from H and $C_1$-$C_3$ alkoxyl;

$R^4$ is chosen from H, $C_1$-$C_6$ alkyl, full-carbon mono-cycloalkyl with 3 to 8 members, heteroalicyclic group with 3 to 8 members, wherein $C_1$-$C_6$ alkyl, full-carbon mono-cycloalkyl with 3 to 8 members, and heteroalicyclic group with 3 to 8 members optionally further substituted by one or more substituent(s) selected from $C_1$-$C_6$ alkyl, $C_1$-$C_6$ alkoxyl, heteroalicyclic group with 3 to 8 members, $C_6$-$C_{10}$ aryl, $C_5$-$C_{10}$ heteroaryl or hydroxyl; and $R^5$ is chosen from H, F, Cl, Br, I, CN, $C_{1-3}$ alkyl, or $C_{1-3}$ haloalkyl.

Alkyl represents linear or branched saturated hydrocarbonyl with a certain number of carbon atoms, and either substituted or not. The alkyl of this invention normally has 1-6 carbon atoms, preferably 1-4 carbon atoms, and most preferably 1-3 carbon atoms. Typical alkyl includes, but is not limited to, methyl, ethyl, n-propyl, isopropyl, n-butyl, isobutyl, tert-butyl, n-pentyl, isopentyl, neopentyl, n-hexyl, isohexyl, 2,2-dimethyl butyl, and 2,3-dimethyl butyl.

Alkylidene represents itself or part of another substituent, i.e. a linear saturated or unsaturated alkyl dimethyl with two terminal monovalent group centers, which is obtained by removing a hydrogen atom each from two terminal carbon of the linear parent alkyl, alkenyl or alkynyl. A typical alkylidene includes, but is not limited to, methylene, ethylidene, vinylidene, ethynylene, propylidene, butylidene, etc.

Alkoxyl represents —O-alkyl, wherein alkyl is as defined herein. It is typically $C_1$-$C_6$ alkoxyl, preferably $C_1$-$C_3$ alkoxyl, including, but not limited to, methoxyl and ethoxyl.

Halogen or halogen group is fluorine, chlorine, bromine or iodine, preferably fluorine, chlorine and bromine. $C_{1-3}$ alkylogen represents alkyl with one or more hydrogen(s) replaced by halogen, preferably one, two or three halogen group(s).

Full-carbon mono-cycloalkyl with 3 to 8 members includes, but is not limited to, cyclopropane, cyclobutane, cyclopentane, and cyclohexane.

Heteroalicyclic group represents a single ring or fused ring containing one or more heteroatom(s) such as N, O or S. It is typically heteroalicyclic group with 3 to 8 members containing one or more heteratom(s) such as N, O or S, preferably heterocyclic group with 3 to 6 members containing one or more heteratoms such as N, O or S, for example epoxypropane, epoxybutane, piperazidine subgroup, morpholino, piperidine subgroup, pyrolidine, and derivatives thereof.

Piperazidine group represents group with the following chemical structure:

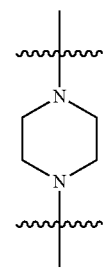

Morpholino represents group with the following chemical structure:

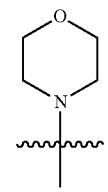

Thiomorpholine group represents group with the following chemical structure:

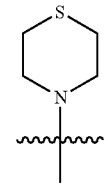

Piperidinyl represents group with the following chemical structure:

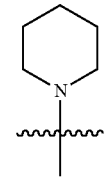

Pyrrolidyl represents group with the following chemical structure:

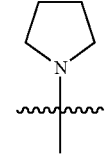

"Aryl" represents full-carbon single ring or fused polycyclic group with 6-10 carbon atoms and completely conjugated π electron system. "Aryl" includes benzene, naphthalin, etc., and aryl may be substituted or not.

"Heteroaryl" represents single ring or fused polycyclic group with 5 to 10 cyclic atoms, containing one, two, three, or four cyclic heteroatom chosen from N, O or S. The remaining atom is C. Additionally, it has completely conjugated π electron system. Heteroaryl includes, but is not limited to, pyrrole, furane, thiophene, imidazole, oxazole, isoxazole, thiazole, pyrazole, triazole, pyridine, pyridone, pyrimidine, pyrazine, pyridazine, indole, indazole, azaindole, benzimidazole, indoline, molindone, quinoline, isoquinoline, quinazoline, benzofuran, benzimidazole, benzoxazole, thienopyridine, thienopyrimidine, etc. Preferable examples of such groups are pyrrole, furane, thiophene, imidazole, oxazole, isoxazole, thiazole, pyrazole, triazole, pyridine, pyridone, pyrimidine, indole, molindone, and quinoline.

In a preferable scheme,

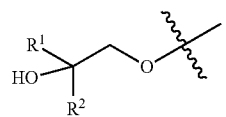

and $R^3$ is located at 6- and 7- of the quinolyl ring, or 7- and 6- of the quinolyl ring, respectively.

More preferably, $R^1$ and $R^2$ are chosen from H and $C_1$-$C_3$ alkyl, and $R^1$ and $R^2$ may not both be simultaneously.

Most preferably, $R^1$ and $R^2$ are methyl. $R^3$ is chosen from H and methoxyl.

In a preferable scheme, $R^4$ is chosen from H, $C_1$-$C_6$ alkyl, full-carbon mono-cycloalkyl with 3 to 8 members, $C_1$-$C_6$ alkylidene substituted by heteroalicyclic group with 3 to 8 members, $C_1$-$C_6$ alkoxyl-$C_1$-$C_6$ alkylidene, or $C_6$-$C_{10}$ aryl-$C_1$-$C_6$ alkylidene.

More preferably, $R^4$ is chosen from hydrogen, methyl, ethyl, propyl, isopropyl, cyclopropyl,

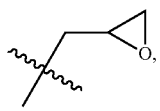

2-methoxyethyl, 2-hydroxyethyl or benzyl.

In a preferable scheme, $R^5$ is chosen from H, F, Cl, Br, I or CN; more preferably, $R^5$ is chosen from H, F, Cl or Br.

6- and 7- of the quinolyl means the substituting positions indicated as below:

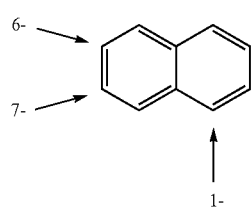

This invention involves, but is not limited to, one of the following compounds, or their stereoisomers, geometric isomers, tautomers, nitrogen oxides, hydrates, solvates, metabolites, pharmaceutically acceptable salts or their prodrugs:

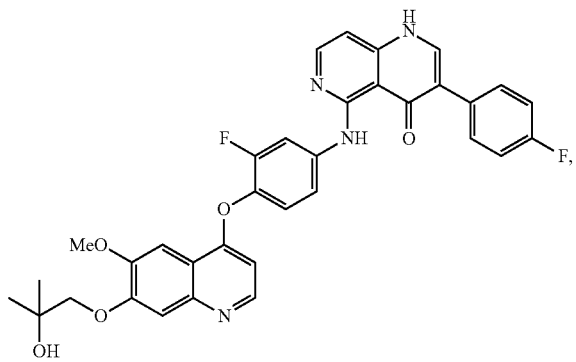

(1)

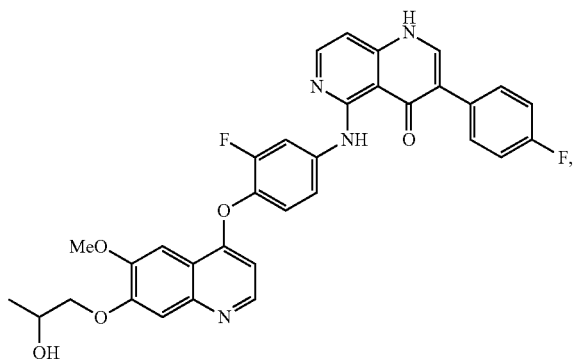

(2)

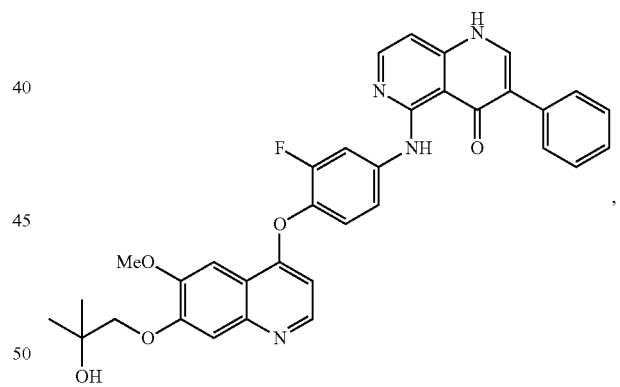

(3)

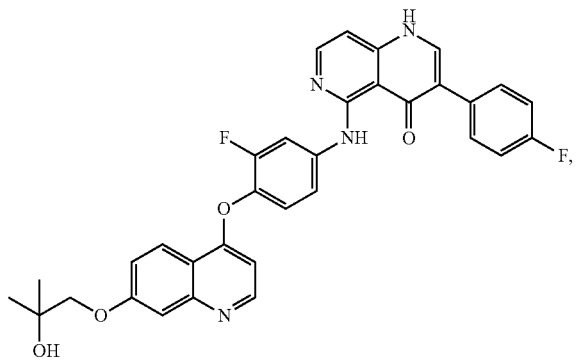

(4)

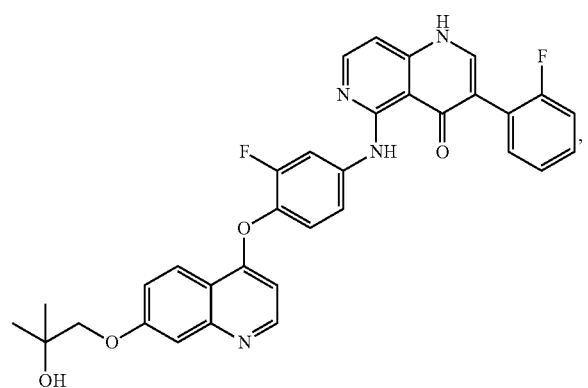
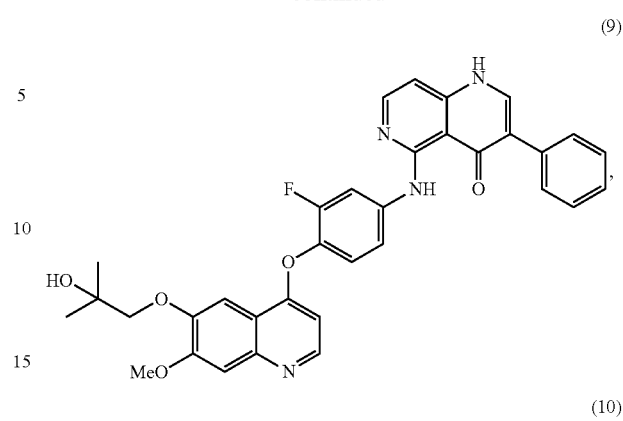
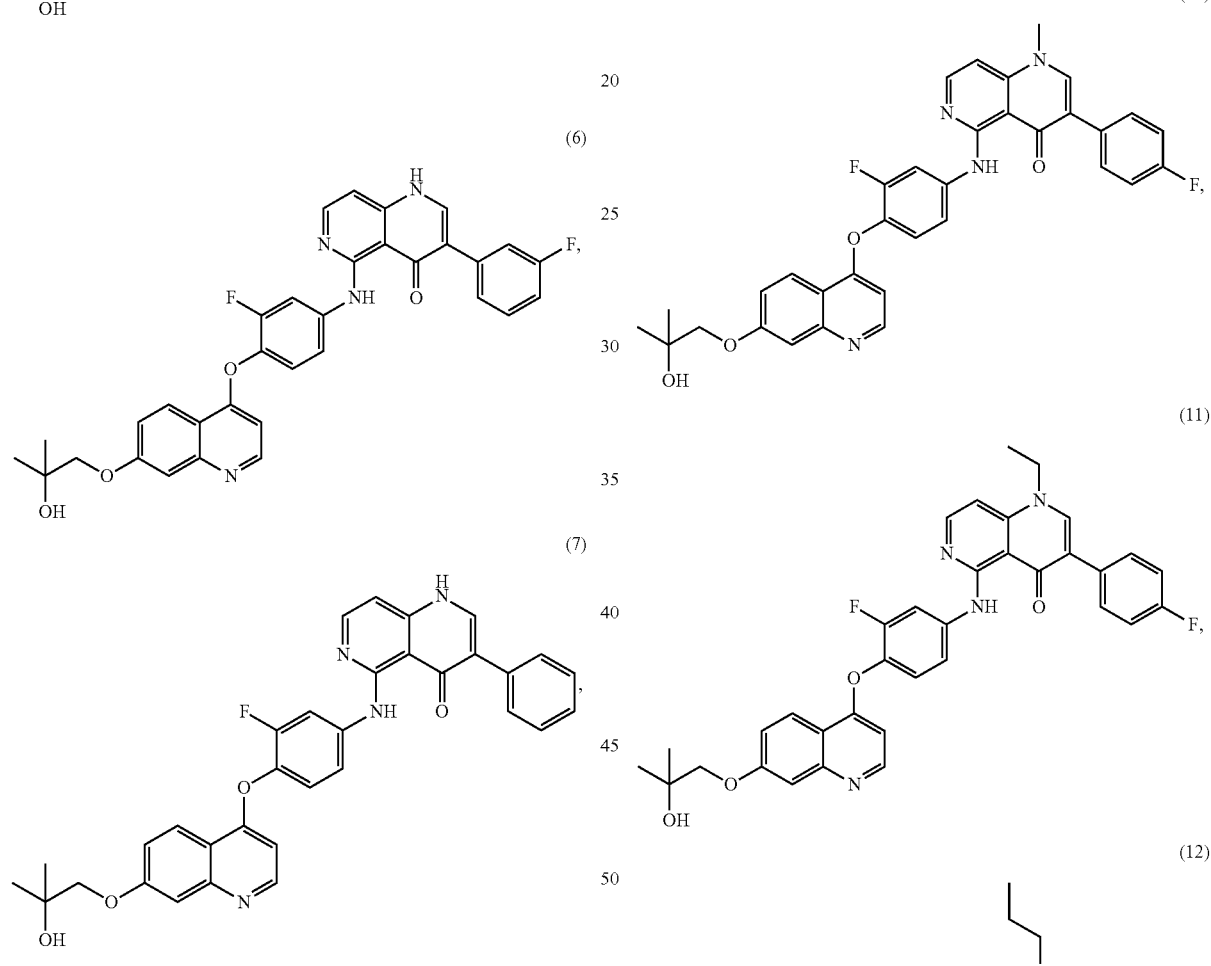
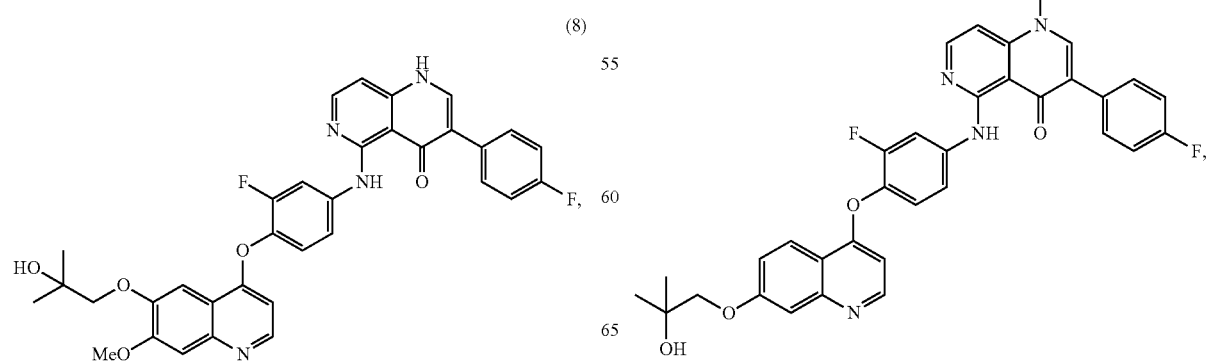

(13)
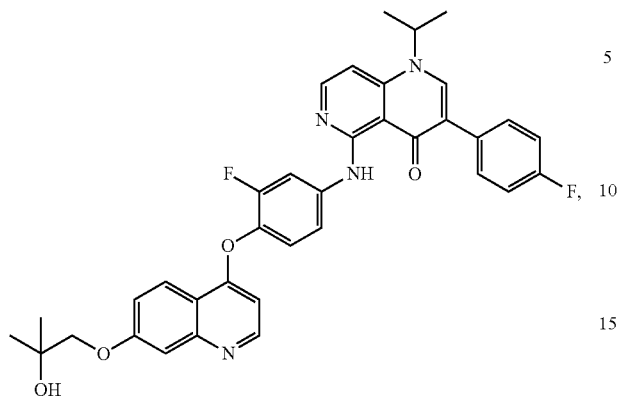

(14)
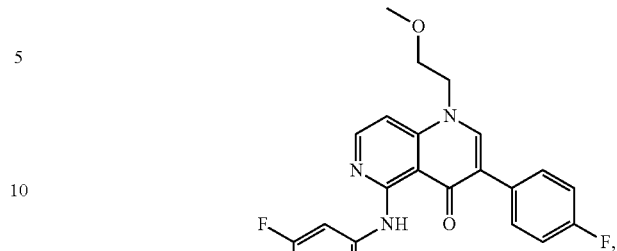

(15)
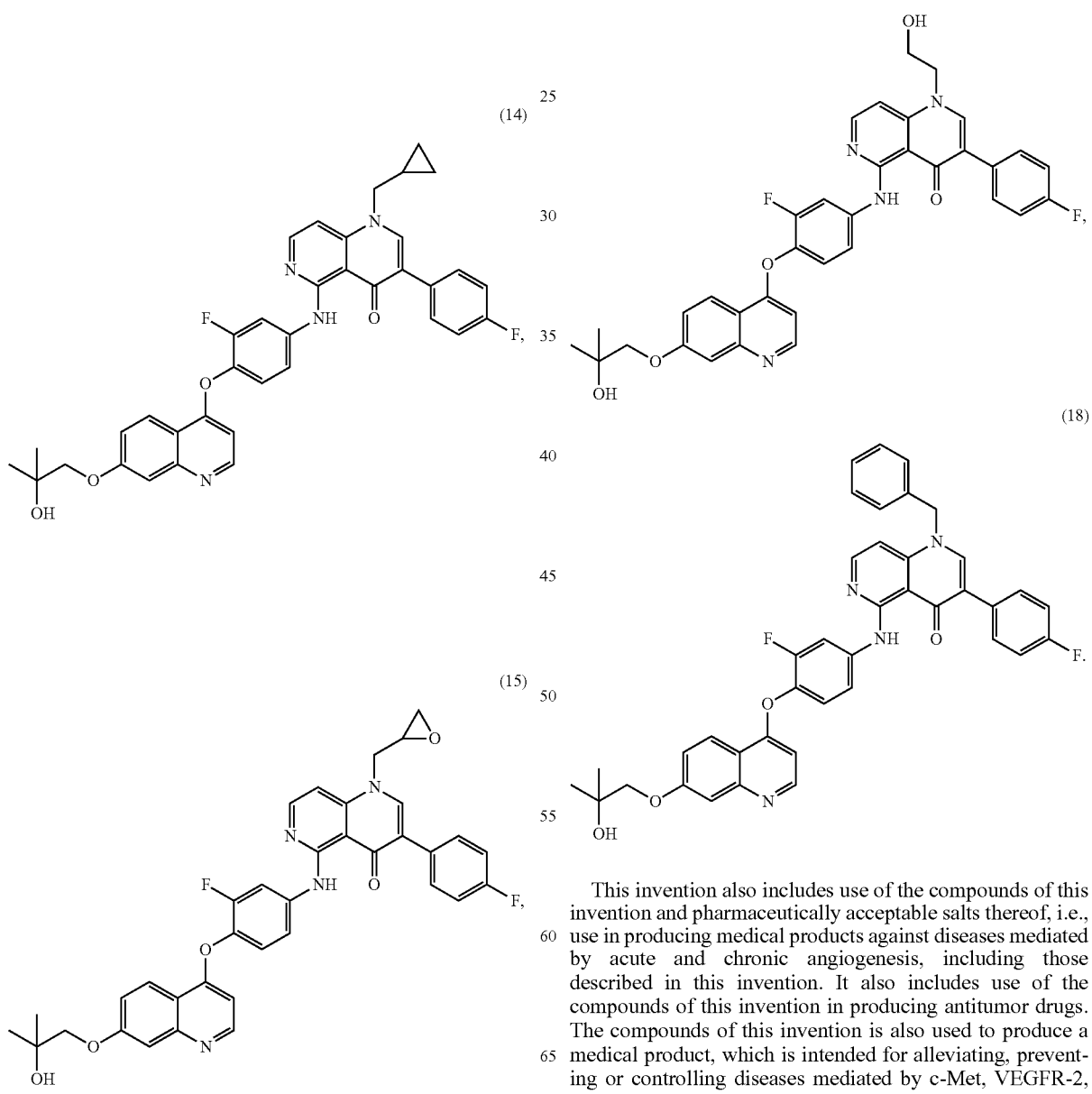

(16)
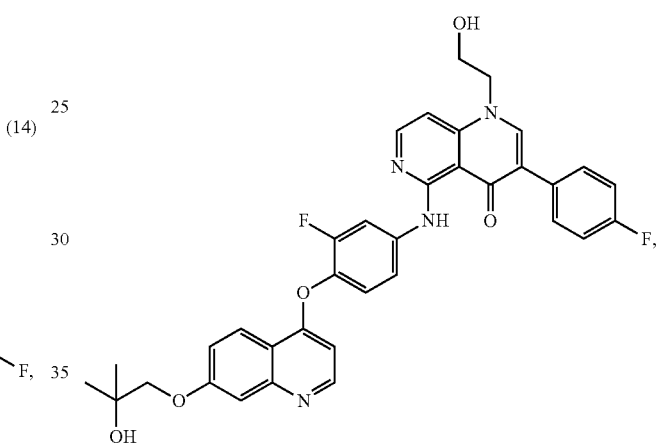

(17)
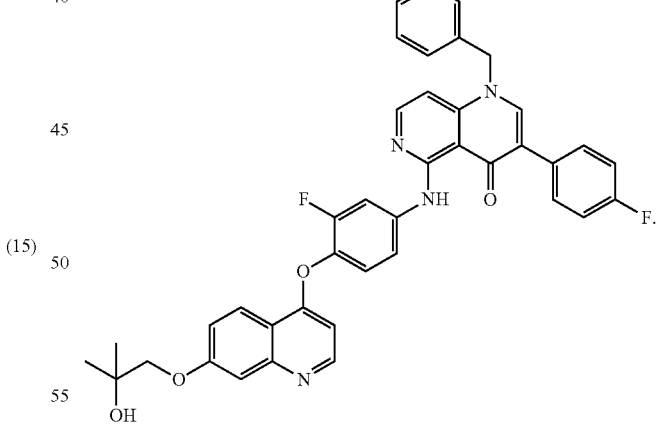

(18)

This invention also includes use of the compounds of this invention and pharmaceutically acceptable salts thereof, i.e., use in producing medical products against diseases mediated by acute and chronic angiogenesis, including those described in this invention. It also includes use of the compounds of this invention in producing antitumor drugs. The compounds of this invention is also used to produce a medical product, which is intended for alleviating, preventing or controlling diseases mediated by c-Met, VEGFR-2, Axl or RET. This invention includes medical combinations which are required therapeutic dose of compounds represented by Formula (I) combined with at least one pharmaceutically acceptable carrier, vehicle or diluent.

This invention also includes regimen which is intended to treat patients with diseases mediated by angiogenesis, or the methods which are sensitive to such diseases. Such methods include treating patients with therapeutic dose of compounds represented by Formula (I).

Unless otherwise specified, all stereoisomers, geometric isomers, tautomers, nitrogen oxides, hydrates, solvates, metabolites and pharmaceutically acceptable prodrugs of the compounds in this invention fall in the scope of this invention.

Specifically, salts are pharmaceutically acceptable salts. The term "pharmaceutically acceptable" means that the substance or compounds must be appropriate chemically and toxicologically, and related to other ingredients of the composition and mammals they are intended for.

If the compounds of this invention are alkaline, then the desirable salts may be prepared through any proper method described in the literature, for example, using inorganic acid, such as hydrochloric acid, hydrobromic acid, sulfuric acid, nitric acid, phosphoric acid, and so on, or using organic acid, such as acetic acid, maleic acid, succinic acid, mandelic acid, fumaric acid, malonic acid, pyruvic acid, oxalic acid, hydroxyacetic acid, and salicylic acid; pyranose acid, such as glucuronic acid and galacturonic acid; α-hydroxy acid, such as citric acid and tartaric acid; amino acids, such as aspartic acid and glutamic acid; aromatic acid, such as benzoic acid and cinnamic acid; sulfonic acid, such as para-toluenesulfonic acid, ethanesulfonic acid, and so on.

If the compounds of this invention are acidic, then the desirable salts may be prepared through appropriate methods, for example, using inorganic or organic alkaline, such as amine (primary amine, secondary amine, tertiary amine), hydroxides of alkalies or alkaline earth metals, and so on. Appropriate salts includes, but are not limited to, organic salts obtained from amino acids, such as glycolamine and arginine, amine, such as primary amine, secondary amine, and tertiary amine, and cyclic amine, such as piperidine, morpholine and piperazidine, and inorganic salts prepared using sodium, calcium, potassium, magnesium, manganum, ferrum, copper, zinc, aluminum and lithium.

Combination, preparation and administration of the compounds in this invention:

In addition, medical combinations of this invention are characterized by including compounds in Formula (I), compounds listed in this invention, or compounds of examples 1-18, and pharmaceutically acceptable carriers, aids, or vehicles. The amount of compounds in the combinations of this invention shows effective and detectable inhibition of protein kinases in biological specimen or patients.

The compounds of this invention may exist in free form, or create proper and pharmaceutically acceptable derivatives. According to this invention, pharmaceutically acceptable derivatives include, but are not limited to, pharmaceutically acceptable prodrugs, salts, esters, salts of esters, or any other adducts or derivatives which may be given indirectly or directly according to patients' demand, and compounds described in other parts of this invention, metabolites or residues thereof.

As described in this invention, pharmaceutically acceptable combinations of this invention further include pharmaceutically acceptable carriers, excipients, or vehicles, such as those that this invention uses, including any solvent, diluent, or other liquid vehicle, dispersant or suspending agent, surfactant, isotonizing agent, thickener, emulsifier, preservative, solid binder or lubricant, and so on, applicable for all target dosage forms. Such as those described as following: In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York. This publication shows that various carriers may be used for preparation of pharmaceutically acceptable combinations and their well-known preparation methods. Except for any conventional carrier which is incompatible with the compounds of this invention, for example any adverse biological effect occurs, or interaction with any other component of the pharmaceutically acceptable combinations happens in an adverse way, their usages are also considered in the this invention.

Usage of the Compounds and Combinations in this Invention:

The medical combinations of this invention are characterized by containing compounds as indicated by Formula (I) or compounds listed in this invention, and pharmaceutically acceptable carriers, aids or vehicles. The amount of the compounds in the combinations of this invention shows effective and detectable inhibition of activities of protein kinases, such as c-Met, VEGFR-2, Axl or RET. The compounds of this invention or combinations thereof will be used as anti-tumor drugs to treat patients or alleviate adverse effect of response to signals such as c-Met, VEGFR-2, Axl or RET.

The compounds of this invention will be used in, but not limited to, prevention or treatment of proliferating disorders among patients by giving effective dose of the compounds of this invention or combinations, especially metastatic cancer, atherosclerosis, and pulmonary fibrosis.

The compounds of this invention will be used to treat tumors including cancer and metastatic cancer, specifically including but not limited to, cancers such as carcinoma of urinary bladder, breast cancer, colon carcinoma, renal carcinoma, hepatoma, lung cancer (including small cell lung cancer), esophageal carcinoma, carcinoma of gallbladder, ovarian cancer, pancreatic cancer, gastric cancer, cancer of the cervix, thyroid cancer, prostatic carcinoma, and cutaneous carcinoma (including squamous carcinoma); hematopoietic cancer of the lymphatic system (including leukemia, acute lymphocystic leukemia, acute lymphoblastic leukemia, B cell lymphoma, T cell lymphoma, Hodgkin's lymphoma, non-Hodgkin's lymphoma, hairy cell leukemia, and Bunkitt's lymphoma); hematopoietic cancer of the bone marrow system (including acute and chronic myeloid granulocytic leukemia, myelodysplastic syndrome, and promyelocytic leukemia); mesenchymal tumor (including fibrosarcoma and rhabdosarcoma, and other tumor carneus, such as soft tissue and cartilage); tumor of central and peripheral nervous system (including astrocytoma, neuroblastoma, neurospongioma, and neurilemmoma); and other tumor (including melanoma, spermocytoma, teratocarcinoma, osteosarcoma, xenoderoma pigmentosum, keratoctanthoma, thyroid follcular carcinoma, and Kaposi sarcoma).

The compounds of this invention may also be used to treat ophthalmic diseases such as corneal graft rejection, ophthalmic neovascularization, corneal neovascularization including trauma or neovascularization after infection; diabetic retinopathy; Terry's syndrome, and neovascular glaucoma; retinal ischemia; vitreous hemorrhage; ulcerative disorders such as gastric ulcer; pathologic but non-malignant conditions, such as hematoma, including infant hemangioendothelioma, angiofibroma of nasopharynx and avascular necrosis; female reproductive system disorder such as mulleriosis. These compounds are also intended to treat hydroncus and conditions with excessive vascular permeability.

The compounds of this invention may be used to manage conditions related to diabetes, such as diabetic retinopathy and microangiopathy. The compounds of this invention are also intended for reduced blood flow among cancer patients. The compounds of this invention may also benefit patients with respect to reduced tumor metastasis.

Besides benefit for human treatment, the compounds of this invention may also be used to treat pets in veterinary area, imported species and farm animals, including mammals, rodents, and so on. Other examples of animals include horses, dogs and cats. In such case, the compounds of this invention include their pharmaceutically acceptable derivatives.

Other characteristics and advantages of this invention will be detailed in the following embodiment section.

Specific embodiments of this invention are detailed as following. It should be understood that the specific embodiments described herein are intended to illustrate and explain this invention only, but not to limit this invention.

Limits of scope or any value revealed herein are not limited this specific scope or value, but rather these limits or value should be considered as values including those close to such as scope or value. For value scope, limits of each scope and individual value may be combined with limits of each scope and individual value to yield one or more new scope of values, which should be considered as reveled herein.

This invention reveals a category of compounds and the preparing methods thereof, intermediates of these compounds and the preparing methods thereof, and use of these compounds as inhibitors of c-Met, VEGFR-2, Axl or RET. Skilled person in this field may prepare them by consulting content of this document and revising process parameters appropriately. It is worth noticing that, all such replacements and revision are obviously for technicians of this field, and are considered as part of this invention. Methods and applications of this invention have been described through preferable embodiments. Those whom it concerns may easily realize and apply technology of this invention by revising or changing and combining methods and applications described herein appropriately without violating any content, principle or scope of this invention.

This invention is further illustrated by combining the Examples as following.

Example 1

Preparation of 5-((3-fluoro-4-((7-(2-hydroxy-2-methylpropoxy)-6-methoxyquinolin-4-yl)oxy)-phenyl)amino)-3-(4-fluorophenyl)-1,6-naphthyridin-4(1H)-one

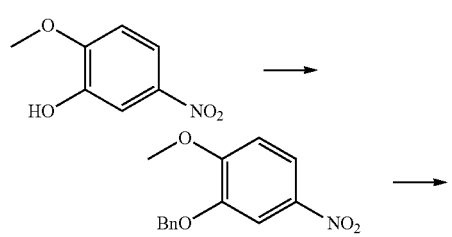

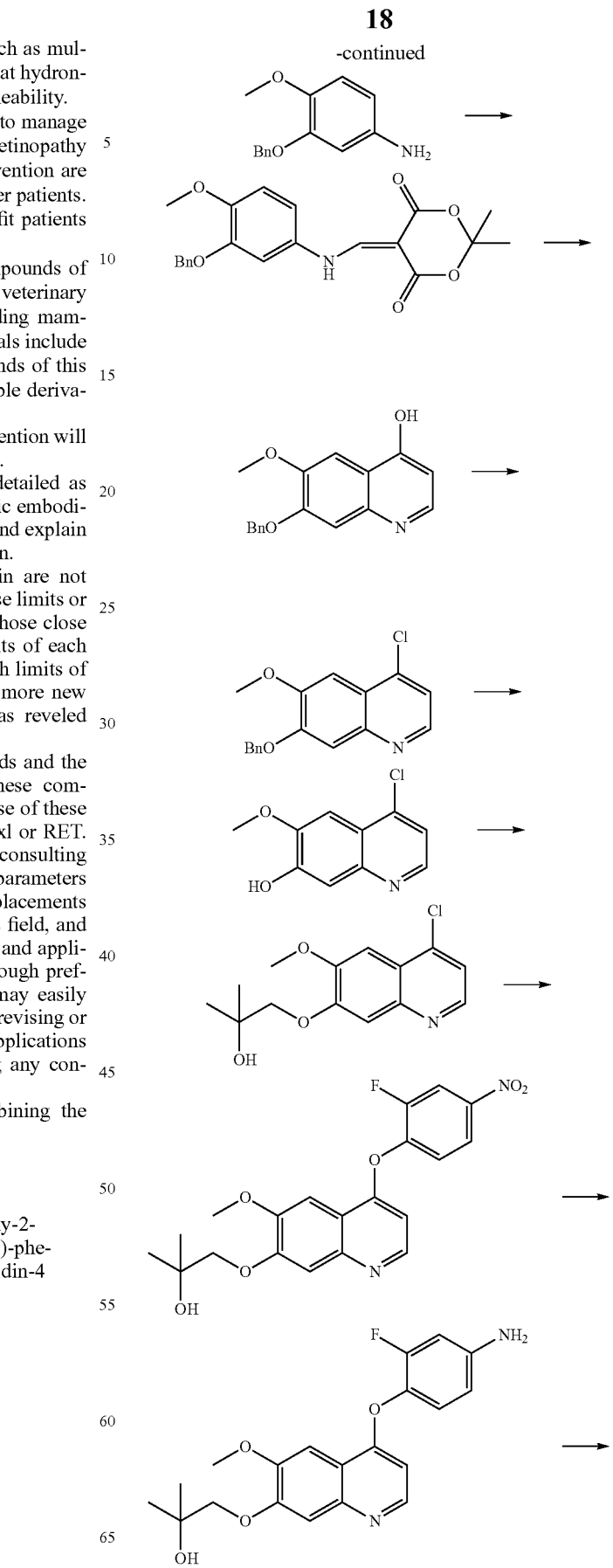

-continued

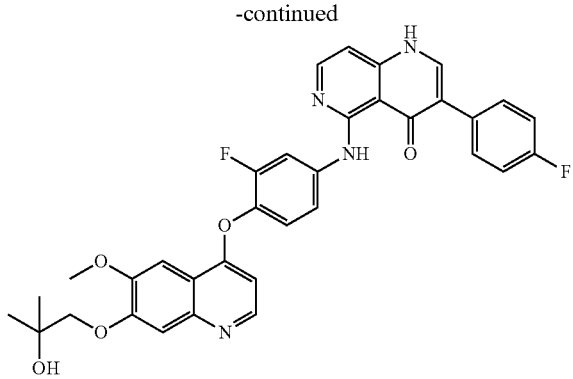

Step 1: Synthesis of 2-benzyloxy-1-methoxyl-4-nitrobenzene

At room temperature, 2-methoxyl-5-nitrophenol (5 g, 29.6 mmol) was dissolved in 60 mL N,N-dimethyl formamide (DMF), and stirred with a magnetic stirring bar, and then anhydrous $K_2CO_3$ (6.1 g, 44.2 mmol) was added. Then benzyl bromide (5.56 g, 32.5 mmol) was added gradually, which was heated to 40° C., allowed to react overnight, and monitored with TLC (petroleum ether:acetone=20:5, $R_f$=0.4). Most of DMF was removed by vacuum distillation. The residue was poured into ice water, then large amount of solid precipitates. The filter cake was washed with alkaline solution, until the solution becomes colorless. The filter cake was dried To afford dark red solid with a yield of 99%.

Step 2: Synthesis of 3-benzyloxy-4-methoxyaniline

Ethanol (72 mL) and water (24 mL) were added into the mixture of 2-benzyloxy-1-methoxyl-4-nitrobenzene (7.1 g, 23.3 mmol) and $NH_4Cl$ (4.4 g, 82.2 mmol) in a pear-shaped flask of 200 mL. At room temperature, iron powder (12.3 g, 219 mmol) were added under stirring, allowed to reflux for 1h, and monitored with TLC (petroleum ether:acetone=20:7, $R_f$=0.4). The reactant were cooled to 50° C., and filter with diatomite. The filtrate was concentrated under vacuum. Water was added and extracted with ethyl acetate. The organic phase was washed with saturated $K_2CO_3$ twice, with water twice, dried with anhydrous sodium sulfate, and concentrated to obtain black solid. The yield was 84%.

Step 3: Synthesis of 5-(((3-benzyloxy)-4-methoxylphenyl)methenyl)-2,2-dimethyl-1,3-dioxane-4,6-dione 3-benzyloxy-4-methoxyaniline (5 g, 21.7 mmol) and malonic acid cyclic isopropylidene ester (3.756 g, 26 mmol) were dissolved in anhydrous ethanol (55 mL). Under stirring, triethyl orthoformate (3.86 g, 26 mmol) was added slowly. The reaction was refluxed for 1h, and large amount of greenish brown solid precipitated. In ice bath, the reactant was stirred for 2h, and filtered. The filter cake was washed with cold anhydrous ethanol, and greenish brown solid was obtained. The yield was 92%.

Step 4: Synthesis of 7-benzyloxy-6-methoxyl-quinolin-4-ol 5-(((3-benzyloxy)-4-methoxylphenyl)methenyl)-2,2-dimethyl-1,3-dioxane-4,6-dione (5 g, 13 mmol) was added into o-dichlorobenzene (40 mL) to obtain a suspension. It was heated to 180° C., and allowed to react for 7h and monitored with TLC (dichlormethane:methanol=20:1, $R_f$=0.2). It was cooled down to room temperature, stirred for 2h, and filtered. The filter cake was washed with cold O-dichlorobenzene, and then with ethyl ether, and dried to obtain khaki solid. The yield was 54%.

Step 5: Synthesis of 7-benzyloxy-4-chloro-6-methoxyl-quinoline 7-benzyloxy-6-methoxyl-quinolin-4-ol (2 g, 7.1 mmol) was added to redistill methyl benzene (10 mL), to obtain a suspension, and redistilled $POCl_3$ (1.1 g, 7.2 mmol) is added slowly. It was heated to 120° C., and allowed to react for 1.5h while being monitored by TLC (petroleum ether: acetone=20:6, $R_f$=0.4). It was cooled down to room temperature. Water was added and pH was adjusted with 3M NaOH solution to 8. Filter was washed with water, and dried to obtain khaki solid. The yield was 90%.

Step 6: Synthesis of 4-chloro-6-methoxylquinolin-7-ol 7-benzyloxy-4-chloro-6-methoxyl-quinoline (1.675 g, 5.58 mmol) and glacial acetic acid (10 mL) were added into a pear-shaped flask of 50 mL. Under stirring, large amount of white solid precipitated. Then aqueous solution of bromide hydrogen (40%, 10 mL) was added into the reactant, which was heated to 80° C. and allowed to react for 3h. The reaction system was cooled down to around 45° C., poured into 80 mL ethyl ether, and stirred. Large amount of white solid precipitated, and was filtered, washed with ethyl ether, and vacuum dried to obtain white solid. The yield was 80%.

Step 7: Synthesis of 1-((4-chloro-6-methoxyquinolin-7-yl)oxy)-2-methylpropan-2-ol 4-chloro-6-methoxylquinolin-7-ol (50 mg, 0.24 mmol) was dissolved in mixed THF/H2O solvent (3 mL, THF/H2O=1:1, V/V), and NaOH (30 mg, 0.75 mmol) and 2-methyloxirane (172 mg, 2.4 mmol) were added successively. At 45° C., stirred for 72 h, and diluted with ethyl ether. The stock solution was washed with 1N NaOH (10 mL×4), and then washed with saturated saline, and the organic phase was dried with anhydrous sodium sulfate. Purify through column chromatography (TLC, petroleum ether:acetone=20:5, $R_f$=0.45), to obtain white solid. The yield was 42.4%.

Step 8: Synthesis of 1-((4-(2-fluoro-4-nitrophenoxy)-6-methoxyquinolin-7-yl)oxy)-2-methylpropan-2-ol 1-((4-chloro-6-methoxyquinolin-7-yl)oxy)-2-methylpropan-2-ol (570 mg, 2.02 mmol) and 2-fluoro-4-nitrophenol (475 mg, 3.02 mmol) were suspended in redistilled toluene (10 mL), then N,N-diisopropylethylamine (DIPEA, 520 mg, 4.03 mmol) was added. The resulted mixture was allowed to react at 120° C. for 48h. The reactant was diluted with ethyl ether, then the organic phase was washed with 1N NaOH, and then with saturated saline, and dried with anhydrous sodium sulfate. The residue was purified by column chromatography (TLC, petroleum ether:acetone=20:8, $R_f$=0.3), to obtain gray solid. The yield was 53%.

Step 9: Synthesis of 1-((4-(4-amino-2-fluorophenoxy)-6-methoxyquinolin-7-yl)oxy)-2-methyl-propan-2-ol 1-((4-(2-fluoro-4-nitrophenoxy)-6-methoxyquinolin-7-yl)oxy)-2-methylpropan-2-ol (410 mg, 1.02 mmol), ammonium chloride (163 mg, 3.05 mmol), and a solution of ethanol:$H_2O$=3:1 (12 mL) were added into a pear-shaped flask of 25 mL, and iron powder (399 mg, 7.125 mmol) was added. The resulted mixture was allowed to react at 80° C. for 1 h. It was cooled down to around 50° C., and filtered with diatomite. The filter cake was washed with ethyl ether. The stock solution was extracted with ethyl ether. The organic phase was combined, dried with anhydrous sodium sulfate, and purified by column chromatography, to obtain khaki solid. The yield was 84%.

Step 10: Synthesis of 5-((3-fluoro-4-((7-(2-hydroxy-2-methylpropoxy)-6-methoxyquinolin-4-yl)-oxy)phenyl)amino)-3-(4-fluorophenyl)-1,6-naphthyridin-4(1H)-one 1-((4-(4-amino-2-fluorophenoxy)-6-methoxyquinolin-7-yl)oxy)-2-methyl-propan-2-ol (60 mg, 0.16 mmol) and 5-chloro-3-(4-fluorophenyl)-1,6-naphthyridin-4(1H)-one (44 mg, 0.16 mmol) were added into a pear-shaped flask of 25 mL. Then isopropanol (6 mL) was added. Under stirring, para-toluenesulfonic acid monohydrate (PTSA.H2O, 37 mg, 0.195 mmol) was added. It was heated to 90° C., and allowed to react for 1 h. Any insoluble material was filtered. The filter cake was washed with isopropanol, to obtain white solid. $^1$H NMR (600 MHz, DMSO-$d_6$): δ 13.40 (s, 1H), 12.96 (s, 1H), 8.88 (d, J=6.3 Hz, 1H), 8.23-8.33 (m, 2H), 8.11 (d, J=6.0 Hz, 1H), 7.79 (s, 1H), 7.77-7.71 (m, 2H), 7.69 (s, 1H), 7.68-7.63 (m, 1H), 7.61 (d, J=8.4 Hz, 1H), 7.29 (t, J=8.4 Hz, 2H), 7.17 (d, J=4.2 Hz, 1H), 7.01 (d, J=5.7 Hz, 1H), 4.07 (s, 3H), 3.99 (s, 2H), 1.29 (s, 6H).

Example 2

Preparation of 5-((3-fluoro-4-((7-(2-hydroxypropoxy)-6-methoxyquinolin-4-yl)oxy)phenyl)-amino)-3-(4-fluorophenyl)-1,6-naphthyridin-4(1H)-one

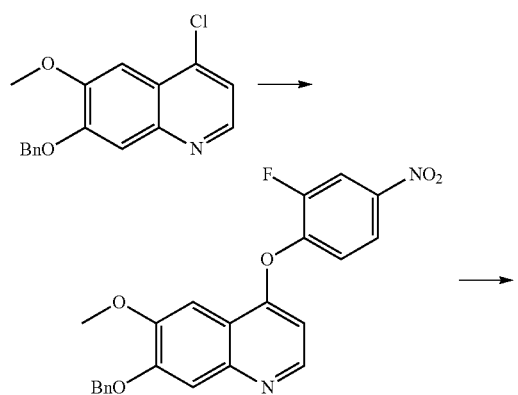

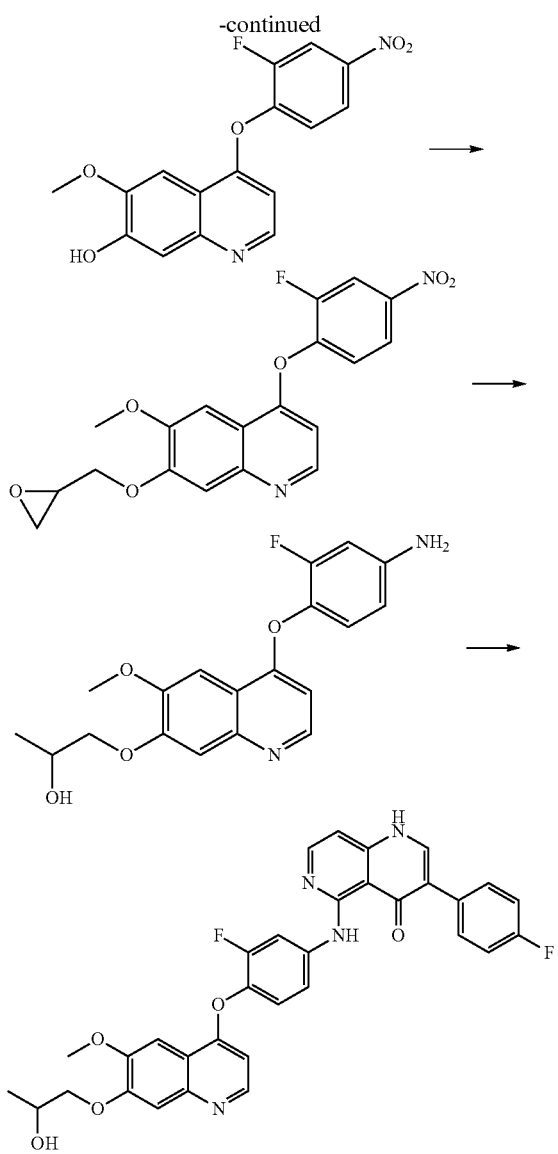

Step 1: Synthesis of 7-(benzyloxy)-4-(2-fluoro-4-nitrophenoxy)-6-methoxyquinoline Redistilled toluene (25 mL) was added into 7-(benzyloxy)-4-chloro-6-methoxyquinoline (2.5 g, 8.3 mmol) and 2-fluoro-4-nitrophenol (2.6 g, 16.6 mmol). While magnetic stirring, added DIPEA (2.7 g, 20.9 mmol). It was heated to 120° C., allowed to reflux react for 48h, and monitored with TLC (petroleum ether:acetone=20:8, Rf=0.4). Then it was cooled down to room temperature, and 200 mL ethyl ether was added. The organic phase was washed with 1M NaOH solution, until the aqueous phrase was colorless. The organic phase was dried with anhydrous sodium sulfate, and the organic phase was concentrated. The residue was recrystallized by ethyl ether, to obtain khaki solid. The yield was 80%.

Step 2: Synthesis of 4-(2-fluoro-4-nitrophenoxy)-6-methoxyquinolin-7-ol 10 mL Glacial acetic acid was added into 7-(benzyloxy)-4-(2-fluoro-4-nitrophenoxy)-6-methoxy-quinoline (1.5 g, 3.6 mmol). Stirred until large amount of white solid was observed. Then aqueous solution of bromide hydrogen (40%, 10 mL) was added. It was heated to 80° C., allowed to react for 4 h, and monitored by TLC (dichloromethane: methanol=40:1, Rf=0.2). It was cooled down to room temperature. The reactant was poured into 100 mL ethyl ether, and stirred for 2h. After filtering, the filter cake was washed with ethyl ether, to obtain white solid. The yield was 90%.

Step 3: Synthesis of 4-(2-fluoro-4-nitrophenoxy)-6-methoxy-7-(oxiran-2-ylmethoxy)quinoline 4-(2-fluoro-4-nitrophenoxy)-6-methoxyquinolin-7-ol (500 mg, 1.51 mmol) and anhydrous potassium carbonate (627 mg, 4.54 mmol) were added into a pear-shaped flask of 25 mL, and then DMF (13 mL) and 2-(chloromethyl)oxirane (700 mg, 7.56 mmol) were added. It was heated to 80° C., and allowed to react for 10 hours. It was cooled down to room temperature, poured into water, and extracted with ethyl ether. The organic phase was combined and dried. After the solvent was removed, the residue was purified by column chromatography, to obtain yellowish solid. The yield was 30%.

Step 4: Synthesis of 1-((4-(4-amino-2-fluorophenoxy)-6-methoxyquinolin-7-yl)oxy)propan-2-ol 4-(2-fluoro-4-nitrophenoxy)-6-methoxy-7-(oxiran-2-ylmethoxy)quinoline (146 mg, 0.378 mmol) was dissolved in a mixed solvent of methanol (10 mL) and dichlormethane (15 mL). Under stirring, Pd/C (30 mg) was added. Under hydrogen atmosphere and at room temperature, it was allowed to react overnight. After the solvent was removed, the residue was purified by column chromatography, to obtain yellowish solid. The yield was 63%.

Step 5: Synthesis of 5-((3-fluoro-4-((7-(2-hydroxypropoxy)-6-methoxyquinolin-4-yl)oxy)phenyl)-amino)-3-(4-fluorophenyl)-1,6-naphthyridin-4(1H)-one 1-((4-(4-amino-2-fluorophenoxy)-6-methoxyquinolin-7-yl)oxy)propan-2-ol and 5-chloro-3-(4-fluorophenyl)-1,6-naphthyridin-4(1H)-one (44 mg, 0.16 mmol) were added into a pear-shaped flask of 10 mL, and then isopropanol (4 mL) was added. Under stirring, PTSA.H2O (38 mg, 0.2 mmol) was added. It was heated to 90° C., and allowed to react for 1 hour. After the solvent was removed, the residue was purified by column chromatography, to obtain yellow solid. The yield was 47%. $^1$H NMR (400 MHz, DMSO-d$_6$): δ 13.22 (s, 1H), 12.49 (s, 1H), 8.67 (d, J=6.0 Hz, 1H), 8.44 (d, J=13.6 Hz, 1H), 8.17 (d, J=5.6 Hz, 2H), 7.74-7.68 (m, 2H), 7.67 (s, 1H), 7.56 (d, J=8.6 Hz, 1H), 7.50 (s, 1H), 7.47 (d, J=6.8 Hz, 1H), 7.24 (t, J=8.0 Hz, 2H), 6.88 (d, J=5.4 Hz, 1H), 6.79 (d, J=6.0 Hz, 1H), 5.01 (s, 1H), 4.07-4.08-4.00 (m, 5H), 1.95-1.87 (m, 1H), 1.23 (d, J=5.2 Hz, 3H).

Example 3

Preparation of 5-((3-fluoro-4-((7-(2-hydroxy-2-methylpropoxy)-6-methoxyquinolin-4-yl)oxy)-phenyl)amino)-3-phenyl-1,6-naphthyridin-4(1H)-one The preparation method was similar to Example 1, except that 5-chloro-3-(4-fluorophenyl)-1,6-naphthyridin-4(1H)-one was replaced by 5-chloro-3-phenyl-1,6-naphthyridin-4(1H)-one. $^1$H NMR (600 MHz, DMSO-d$_6$): δ 13.45 (s, 1H), 12.93 (s, 1H), 8.89 (d, J=6.6 Hz, 1H), 8.25-8.34 (m, 2H), 8.11 (d, J=4.8 Hz, 1H), 7.79 (s, 1H), 7.67-7.72 (m, 3H), 7.65 (d, J=8.4 Hz, 1H), 7.62 (d, J=8.4 Hz, 1H), 7.48 (d, J=7.8 Hz, 2H), 7.38 (t, J=7.2 Hz, 1H), 7.17 (d, J=4.2 Hz, 1H), 7.01 (d, J=5.7 Hz, 1H), 4.07 (s, 3H), 3.99 (s, 2H), 1.29 (s, 6H).

Example 4

Preparation of 5-((3-fluoro-4-((7-(2-hydroxy-2-methylpropoxy)quinolin-4-yl)oxy)phenyl)amino)-3-(4-fluorophenyl)-1,6-naphthyridin-4(1H)-one

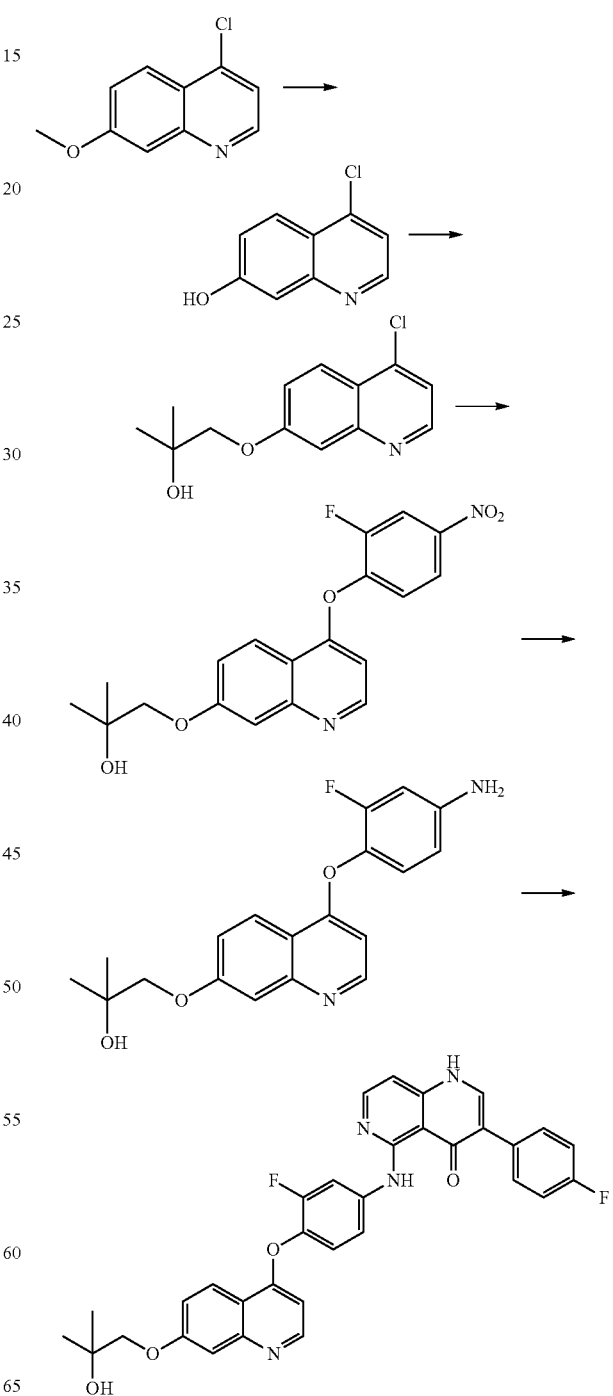

Step 1: Synthesis of 4-chloroquinolin-7-ol

BBr$_3$ (4.9 g, 19.6 mmol) in dichlormethane (15 mL) was added dropwise into 4-chloro-7-methoxylquinoline (0.95 g, 4.9 mmol) in dichlormethane (45 mL) slowly at −70° C. under nitrogen. And then the reactions system was brought to room temperature. Benzyltriethylammonium chloride (TEBA, 0.19 g, 0.83 mmol) in dichlormethane (5 mL) was added. It was stirred at room temperature for 20 h, and monitored with TLC (petroleum ether:acetone=20:5, Rf=0.4). Under stirring in ice bath, icy water (25 mL) was added into the reactant to quench BBr$_3$. Vast majority of dichlormethane was removed, and pH of the remaining solution was adjusted with 1N NaOH to 7. Large amount of white solid precipitates was filtered and dried in vacuum (45° C.) for 24 h, to obtain the title compound. The yield was 90%. $^1$H NMR (600 MHz, DMSO-d$_6$): δ 10.54 (s, 1H), 8.69 (d, J=4.8 Hz, 1H), 8.06 (d, J=9.6 Hz, 1H), 7.51 (d, J=4.8 Hz, 1H), 7.30-7.36 (m, 2H).

Step 2: Synthesis of 1-((4-chloroquinolin-7-yl)oxy)-2-methylpropan-2-ol 4-chloroquinolin-7-ol (100 mg, 0.56 mmol) was dissolved in mixed solvent of THF/H$_2$O (8 mL, THF/H$_2$O=1:1, V/V). NaOH (66.6 mg, 1.67 mmol) and 2-methyloxirane (400 mg, 5.56 mmol) were added successively. At 45° C., the reactant was stirred for 24 h, and diluted with ethyl ether. Then the stock solution was washed with 1N NaOH (10 mL×4), and then with saturated saline. The organic phase was dried with anhydrous sodium sulfate. After the solvent was removed, the residue was purified by column chromatography (TLC, petroleum ether:acetone=20:5, Rf=0.45), to obtain white solid. The yield was 63%. $^1$H NMR (600 MHz, DMSO-d$_6$): δ 7.88 (d, J=4.8 Hz, 1H), 7.22 (d, J=9.0 Hz, 1H), 6.70 (d, J=4.8 Hz, 1H), 6.52-6.57 (m, 2H), 3.88 (s, 1H), 3.06 (s, 2H), 0.41 (s, 6H).

Step 3: Synthesis of 1-((4-(2-fluoro-4-nitrophenoxy)quinolin-7-yl)oxy)-2-methylpropan-2-ol 1-((4-chloroquinolin-7-yl)oxy)-2-methylpropan-2-ol (0.456 g, 1.8 mmol) and 2-fluoro-4-nitrophenol (0.568 g, 3.6 mmol) were suspended in redistilled toluene (20 mL). N,N-diisopropylethylamine (0.583 g, 4.5 mmol) was added to the reactant. It was allowed to react at 120° C. for 30 h in oil bath. The reactant was diluted with ethyl ether. The organic phase was washed with 1N NaOH, and with saturated saline, and then dried with anhydrous sodium sulfate. After the solvent was removed, the residue was purified by column chromatography (TLC, petroleum ether:acetone=20:8, Rf=0.3), to obtain gray solid. The yield was 90%. $^1$H NMR (600 MHz, DMSO-d$_6$): δ 8.72 (d, J=4.8 Hz, 1H), 8.48 (d, J=10.2 Hz, 1H), 8.20 (d, J=9.0 Hz, 1H), 8.16 (d, J=9.0 Hz, 1H), 7.64 (t, J=8.4 Hz, 1H), 7.44 (s, 1H), 7.36 (d, J=9.0 Hz, 1H), 6.80 (d, J=4.8 Hz, 1H), 4.76 (s, 1H), 3.93 (s, 2H), 1.27 (s, 6H).

Step 4: Synthesis of 1-((4-(4-amino-2-fluorophenoxy)quinolin-7-yl)oxy)-2-methylpropan-2-ol 1-((4-(2-fluoro-4-nitrophenoxy)quinolin-7-yl)oxy)-2-methylpropan-2-ol (54 mg, 0.145 mmol) was dissolved in methanol (10 mL). Under stirring, Pd/C (11 mg) was added. It was allowed to react under hydrogen atmosphere at room temperature for 5 h. After the solvent was removed, the residue was purified by column chromatography (TLC, petroleum ether:acetone=20:10, Rf=0.3), to obtain gray solid. The yield was 90%. $^1$H NMR (400 MHz, DMSO-d$_6$): δ 8.55 (d, J=4.2 Hz, 1H), 8.18 (d, J=9.0 Hz, 1H), 7.33 (s, 1H), 7.28 (d, J=9.0 Hz, 1H), 7.06 (t, J=12.0 Hz, 1H), 6.53 (d, J=12.8 Hz, 1H), 6.44 (d, J=8.4 Hz, 1H), 6.38 (d, J=4.8 Hz, 1H), 5.51 (s, 2H), 4.72 (s, 1H), 3.89 (s, 2H), 1.26 (s, 6H).

Step 5: Preparation of 5-((3-fluoro-4-((7-(2-hydroxy-2-methylpropoxy)quinolin-4-yl)oxy)phenyl)amino)-3-(4-fluorophenyl)-1,6-naphthyridin-4(1H)-one 1-((4-(4-amino-2-fluorophenoxy)quinolin-7-yl)oxy)-2-methylpropan-2-ol (40 mg, 0.117 mmol) and 5-chloro-3-(4-fluorophenyl)-1,6-naphthyridin-4(1H)-one (33 mg, 0.12 mmol) were added into a pear-shaped flask of 25 mL. Then isopropanol (8 mL) was added. Under stirring, concentrated hydrochloric acid (1 drop) was added. It was heated to 90° C., and allowed to react for 1 h. The precipitated solid was filtered. The filter cake was dissolved in 10 mL mixed solvent of dichlormethane and methanol. Equivalent amount of triethylamine was added. The reactant was stirred at room temperature for 0.5 h. The precipitated solid was filtered and dried to obtain white solid. The yield was 88%. $^1$H NMR (600 MHz, DMSO-d6): δ 13.41 (s, 2H), 9.03 (d, J=6.0 Hz, 1H), 8.54 (d, J=9.0 Hz, 1H), 8.30 (d, J=3.6 Hz, 1H), 8.21 (s, 1H), 8.06 (d, J=4.8 Hz, 1H), 7.78 (s, 1H), 7.77-7.72 (m, 2H), 7.72-7.63 (m, 2H), 7.59 (d, J=8.4 Hz, 1H), 7.33 (s, 1H), 7.29 (t, J=8.4 Hz, 2H), 7.10 (d, J=5.4 Hz, 1H), 4.00 (s, 2H), 1.29 (s, 6H).

Example 5

Preparation of 5-((3-fluoro-4-((7-(2-hydroxy-2-methylpropoxy)quinolin-4-yl)oxy)phenyl)amino)-3-(2-fluorophenyl)-1,6-naphthyridin-4(1H)-one The preparation method was similar to Example 4, except that 5-chloro-3-(4-fluorophenyl)-1,6-naphthyridin-4(1H)-one was replaced with 5-chloro-3-(2-fluorophenyl)-1,6-naphthyridin-4(1H)-one. $^1$H NMR (600 MHz, DMSO-d$_6$): δ 13.22 (s, 1H), 13.08 (s, 1H), 8.98 (d, J=3.0 Hz, 1H), 8.53 (d, J=8.4 Hz, 1H), 8.43 (d, J=11.4 Hz, 1H), 8.15-8.24 (m, 2H), 7.79 (s, 1H), 7.64 (d, J=7.8 Hz, 1H), 7.55-7.75 (m, 2H), 7.48-7.54 (m 1H), 7.43-7.47 (m, 1H), 7.26-7.33 (m, 2H), 7.07-7.12 (m, 1H), 7.01-7.06 (m, 1H), 4.00 (s, 2H), 1.29 (s, 6H).

Example 6

Preparation of 5-((3-fluoro-4-((7-(2-hydroxy-2-methylpropoxy)quinolin-4-yl)oxy)phenyl)amino)-3-(3-fluorophenyl)-1,6-naphthyridin-4(1H)-one The preparation method was similar to Example 4, except that 5-chloro-3-(4-fluorophenyl)-1,6-naphthyridin-4(1H)-one was replaced with 5-chloro-3-(3-fluorophenyl)-1,6-naphthyridin-4(1H)-one. $^1$H NMR (600 MHz, DMSO-d$_6$): δ 13.35 (s, 2H), 9.03 (d, J=6.6 Hz, 1H), 8.54 (d, J=9.0 Hz, 1H), 8.37 (d, J=5.4 Hz, 1H), 8.25 (d, J=12.6 Hz, 1H), 8.09 (d, J=6.0 Hz, 1H), 7.77 (s, 1H), 7.63-7.72 (m, 2H), 7.57-7.66 (m, 2H), 7.57 (d, J=7.8 Hz, 1H), 7.49 (dd, J=14.4, 7.2 Hz, 1H), 7.25-7.33 (m, 1H), 7.21 (t, J=8.4 Hz, 1H), 7.10 (d, J=6.3 Hz, 1H), 4.00 (s, 2H), 1.29 (s, 6H).

Example 7

Preparation of 5-((3-fluoro-4-((7-(2-hydroxy-2-methylpropoxy)quinolin-4-yl)oxy)phenyl)amino)-3-phenyl-1,6-naphthyridin-4(1H)-one The preparation method was similar to Example 4, except that 5-chloro-3-(4-fluorophenyl)-1,6-naphthyridin-4(1H)-one was replaced with 5-chloro-3-phenyl-1,6-naphthyridin-4(1H)-one. $^1$H NMR (600 MHz, DMSO-d$_6$): δ 13.45 (s, 1H), 13.27 (s, 1H), 9.03 (d, J=6.6 Hz, 1H), 8.54 (d, J=9.3 Hz, 1H), 8.28 (d, J=5.4 Hz, 1H), 8.24 (d, J=9.3 Hz, 1H), 8.07 (d, J=6.0 Hz, 1H), 7.77 (s, 1H), 7.68-7.73 (m, 3H), 7.66 (d, J=9.6 Hz, 1H), 7.60 (d, J=8.4 Hz, 1H), 7.46 (t, J=7.5, 7.5 Hz, 2H), 7.38 (t, J=7.2, 1H), 7.24-7.33 (m, 1H), 7.08 (d, J=6.0 Hz, 1H), 4.00 (s, 2H), 1.29 (s, 6H).

Example 8

Preparation of 5-((3-fluoro-4-((6-(2-hydroxy-2-methylpropoxy)-7-methoxyquinolin-4-yl)oxy)-phenyl)amino)-3-(4-fluorophenyl)-1,6-naphthyridin-4(1H)-one The preparation method was similar to Example 1, except that 2-methoxyl-5-nitrophenol was replaced with 2-methoxyl-4-nitrophenol. $^1$H NMR (600 MHz, DMSO-d$_6$): δ 13.38 (s, 1H), 12.90 (s, 1H), 8.87 (d, J=6.0 Hz, 1H), 8.31 (d, J=9.0 Hz, 1H), 8.26 (d, J=3.6 Hz, 1H), 8.12 (d, J=4.2 Hz, 1H), 7.81 (s, 1H), 7.71-7.76 (m, 1H), 7.68 (s, 1H), 7.58-7.64 (m, 1H), 7.49 (d, J=7.2 Hz 1H), 7.28 (t, J=8.4 Hz, 2H), 7.10-7.16 (m, 2H), 7.00 (d, J=4.8 Hz, 1H), 4.07 (s, 3H), 4.02 (s, 2H), 1.27 (s, 6H).

Example 9

Preparation of 5-((3-fluoro-4-((6-(2-hydroxy-2-methylpropoxy)-7-methoxyquinolin-4-yl)oxy)-phenyl)amino)-3-phenyl-1,6-naphthyridin-4(1H)-one The preparation method was similar to Example 1, except that 2-methoxyl-5-nitrophenol was replaced with 2-methoxyl-4-nitrophenol, and 5-chloro-3-(4-fluorophenyl)-1,6-naphthyridin-4(1H)-one was replaced with 5-chloro-3-phenyl-1,6-naphthyridin-4(1H)-one. $^1$H NMR (400 MHz, DMSO-d$_6$): δ 13.39 (s, 1H), 12.85 (s, 1H), 8.85 (d, J=6.8 Hz, 1H), 8.03-8.23 (m, 2H), 8.08 (d, J=6.4 Hz, 1H), 7.78 (s, 1H), 7.67-7.59 (m, 4H), 7.46-7.40 (m, 2H), 7.35 (t, J=7.2 Hz, 1H), 7.15-7.09 (m, 2H), 6.97 (d, J=6.4 Hz, 1H), 4.06 (s, 3H), 4.01 (s, 2H), 1.27 (s, 6H).

Example 10

Preparation of 5-((3-fluoro-4-((7-(2-hydroxy-2-methylpropoxy)quinolin-4-yl)oxy)phenyl)amino)-3-(4-fluorophenyl)-1-methyl-1,6-naphthyridin-4(1H)-one 5-((3-fluoro-4-((7-(2-hydroxy-2-methylpropoxy)quinolin-4-yl)oxy)phenyl)amino)-3-(4-fluorophenyl)-1,6-naphthyridin-4(1H)-one (100 mg, 0.13 mmol) and anhydrous potassium carbonate (95 mg, 0.69 mmol) were added into a pear-shaped flask of 10 mL. DMF (3 mL) was added and stirred under stirring for 0.5 h, and then iodomethane (71 mg, 0.52 mmol) was added. After additional stirring for 4h, the reactant was poured into water (12 mL). The insoluble material was filtered. The filter cake was washed with water, and dried in vacuum, to obtain pale yellow solid. The yield was 73.5%. $^1$H NMR (400 MHz, DMSO-d$_6$): δ 13.57 (s, 1H), 8.97 (d, J=6.8 Hz, 1H), 8.50 (d, J=9.2 Hz, 1H), 8.40 (s, 1H), 8.35 (d, J=12.8 Hz, 1H), 8.23 (d, J=6.4 Hz, 1H), 7.83-7.69 (m, 3H), 7.68-7.54 (m, 3H), 7.38-7.23 (m, 2H), 7.14 (d, J=5.2 Hz, 1H), 7.04 (d, J=6.4 Hz, 1H), 3.98 (s, 2H), 3.89 (s, 3H), 1.28 (s, 6H).

Example 11

Preparation of 1-ethyl-5-((3-fluoro-4-((7-(2-hydroxy-2-methylpropoxy)quinolin-4-yl)oxy)phenyl)-amino)-3-(4-fluorophenyl)-1,6-naphthyridin-4(1H)-one The preparation method was similar to Example 10, except that iodomethane was replaced with iodoethane. $^1$H NMR (400 MHz, DMSO-d$_6$): δ 13.47 (s, 1H), 8.58 (d, J=5.2 Hz, 1H), 8.37 (dd, J=13.6, 2.0 Hz, 1H), 8.34 (s, 1H), 8.27 (d, J=6.4 Hz, 1H), 8.22 (d, J=8.8 Hz, 1H), 7.74 (d, J=5.6 Hz, 1H), 7.72 (d, J=5.6 Hz, 1H), 7.50 (d, J=8.0 Hz, 1H), 7.41-7.36 (m, 2H), 7.32 (dd, J=9.0, 2.4 Hz, 1H), 7.26 (t, J=8.8 Hz, 2H), 7.04 (d, J=6.4 Hz, 1H), 6.48 (d, J=5.2 Hz, 1H), 4.74 (s, 1H), 4.32 (q, J=7.2 Hz, 2H), 3.91 (s, 2H), 1.39 (t, J=7.2 Hz, 3H), 1.27 (s, 6H).

Example 12

Preparation of 5-((3-fluoro-4-((7-(2-hydroxy-2-methylpropoxy)quinolin-4-yl)oxy)phenyl)amino)-3-(4-fluorophenyl)-1-propyl-1,6-naphthyridin-4(1H)-one The preparation method was similar to Example 10, except that iodomethane was replaced with iodopropane. $^1$H NMR (400 MHz, DMSO-d$_6$): δ 13.45 (s, 1H), 8.58 (d, J=3.6 Hz, 1H), 8.30-8.40 (m, 2H), 8.18-8.28 (m, 2H), 7.66-7.76 (m, 2H), 7.49 (d, J=7.0 Hz, 1H), 7.44-7.34 (m, 2H), 7.20-7.33 (m, 3H), 7.04 (d, J=4.8 Hz, 1H), 6.48 (d, J=5.2 Hz, 1H), 4.71 (s, 1H), 4.17-4.30 (m, 2H), 3.90 (s, 2H), 1.74-1.88 (m, 2H), 1.27 (s, 6H), 0.90-1.02 (m, 3H).

Example 13

Preparation of 5-((3-fluoro-4-((7-(2-hydroxy-2-methylpropoxy)quinolin-4-yl)oxy)phenyl)amino)-3-(4-fluorophenyl)-1-isopropyl-1,6-naphthyridin-4(1H)-one The preparation method was similar to Example 10, except that iodomethane was replaced with 2-iodopropane. $^1$H NMR (400 MHz, DMSO-d$_6$): δ 13.56 (s, 1H), 8.58 (d, J=5.2 Hz, 1H), 8.36 (dd, J=13.6, 2.0 Hz, 1H), 8.26 (d, J=6.4 Hz, 1H), 8.19-8.24 (m, 2H), 7.75-7.66 (m, 2H), 7.49 (d, J=8.0 Hz, 1H), 7.43-7.34 (m, 2H), 7.31 (dd, J=9.2, 2.2 Hz, 1H), 7.23-7.28 (m, 2H), 7.18 (d, J=6.6 Hz, 1H), 6.47 (d, J=5.0 Hz, 1H), 5.06-4.95 (m, 1H), 4.72 (s, 1H), 3.90 (s, 2H), 1.53 (d, J=6.4 Hz, 6H), 1.27 (s, 6H).

Example 14

Preparation of 1-cyclopropyl-5-((3-fluoro-4-((7-(2-hydroxy-2-methylpropoxy)quinolin-4-yl)oxy)-phenyl)amino)-3-(4-fluorophenyl)-1,6-naphthyridin-4(1H)-one The preparation method was similar to Example 10, except that iodomethane was replaced with (bromomethyl)

cyclopropane. $^1$H NMR (400 MHz, DMSO-d$_6$): δ 13.46 (s, 1H), 8.57 (d, J=5.2 Hz, 1H), 8.40-8.32 (m, 2H), 8.26 (d, J=6.0 Hz, 1H), 8.21 (d, J=9.0 Hz, 1H), 7.71 (d, J=5.6 Hz, 1H), 7.69 (d, J=5.8 Hz, 1H), 7.50 (d, J=8.2 Hz, 1H), 7.40 (d, J=9.0 Hz, 1H), 7.36 (d, J=2.0 Hz, 1H), 7.30 (dd, J=9.2, 2.0 Hz, 1H), 7.20-7.28 (m, 2H), 7.13 (d, J=6.2 Hz, 1H), 6.47 (d, J=5.0 Hz, 1H), 4.71 (s, 1H), 4.17 (d, J=6.8 Hz, 1H), 3.90 (s, 2H), 1.41-1.32 (m, 1H), 1.26 (s, 6H), 0.53-0.60 (m, 2H), 0.48-0.52 (m, 2H).

Example 15

Preparation of 5-((3-fluoro-4-((7-(2-hydroxy-2-methylpropoxy)quinolin-4-yl)oxy)phenyl)amino)-3-(4-fluorophenyl)-1-(oxiran-2-ylmethyl)-1,6-naphthyridin-4(1H)-one The preparation method was similar to Example 10, except that iodomethane was replaced with 2-(bromomethyl)oxirane. $^1$H NMR (400 MHz, DMSO-d$_6$): δ 13.14 (s, 1H), 8.55 (d, J=5.2 Hz, 1H), 8.34-8.16 (m, 3H), 7.56 (s, 1H), 7.54 (d, J=5.4 Hz, 1H), 7.52 (d, J=5.4 Hz, 1H), 7.46-7.40 (m, 1H), 7.38 (d, J=2.4 Hz, 1H), 7.28-7.21 (m, 2H), 7.20-7.14 (m, 1H), 7.13-7.09 (m, 1H), 6.63 (d, J=6.2 Hz, 1H), 6.44 (d, J=5.2 Hz, 1H), 4.51 (dd, J=15.6, 5.6 Hz, 1H), 4.03 (dd, J=15.6, 5.6 Hz, 1H), 3.96 (s, 2H), 3.42-3.35 (m, 1H), 2.97-2.92 (m, 1H), 2.62-2.56 (m, 1H), 1.40 (s, 6H).

Example 16

Preparation of 5-((3-fluoro-4-((7-(2-hydroxy-2-methylpropoxy)quinolin-4-yl)oxy)phenyl)amino)-3-(4-fluorophenyl)-1-(2-methoxyethyl)-1,6-naphthyridin-4(1H)-one The preparation method was similar to Example 10, except that iodomethane was replaced with 1-bromo-2-methoxyethane. $^1$H NMR (400 MHz, DMSO-d$_6$): δ 13.44 (s, 1H), 8.59 (d, J=5.2 Hz, 1H), 8.37 (dd, J=13.6, 2.0 Hz, 1H), 8.26 (d, J=6.0 Hz, 1H), 8.24-8.19 (m, 2H), 7.71 (d, J=5.6 Hz, 1H), 7.69 (d, J=6.0 Hz, 1H), 7.51 (dd, J=9.2, 1.2 Hz, 1H), 7.41 (d, J=9.0 Hz, 1H), 7.37 (d, J=2.4 Hz, 1H), 7.31 (dd, J=9.2, 2.4 Hz, 1H), 7.23-7.29 (m, 2H), 7.08 (d, J=6.4 Hz, 1H), 6.48 (d, J=5.2 Hz, 1H), 4.73 (s, 1H), 4.49 (t, J=4.2, 4.0 Hz, 2H), 3.91 (s, 2H), 3.70 (t, J=4.2, 4.0 Hz, 2H), 3.26 (s, 3H), 1.27 (s, 6H).

Example 17

Preparation of 5-((3-fluoro-4-((7-(2-hydroxy-2-methylpropoxy)quinolin-4-yl)oxy)phenyl)amino)-3-(4-fluorophenyl)-1-(2-hydroxyethyl)-1,6-naphthyridin-4(1H)-one The preparation method was similar to Example 10, except that iodomethane was replaced with 2-bromoethanol. $^1$H NMR (400 MHz, DMSO-d$_6$): δ 13.65 (s, 1H), 8.99 (d, J=6.4 Hz, 1H), 8.50 (d, J=9.2 Hz, 1H), 8.37-8.26 (m, 2H), 8.16 (d, J=6.2 Hz, 1H), 7.73 (d, J=6.2 Hz, 1H), 7.71 (d, J=5.6 Hz, 1H), 7.67 (s, 1H), 7.62 (d, J=8.8 Hz, 2H), 7.59 (d, J=4.8 Hz, 1H), 7.32-7.23 (m, 2H), 7.19 (d, J=6.4 Hz, 1H), 7.14 (d, J=6.0 Hz, 1H), 5.15 (br), 4.51-4.37 (m, 2H), 3.98 (s, 2H), 3.82-3.71 (m, 2H), 1.27 (s, 6H).

Example 18

Preparation of 1-benzyl-5-((3-fluoro-4-((7-(2-hydroxy-2-methylpropoxy) quinolin-4-yl)oxy)phenyl)-amino)-3-(4-fluorophenyl)-1,6-naphthyridin-4(1H)-one The preparation method was similar to Example 10, except that iodomethane was replaced with benzyl bromide. $^1$H NMR (400 MHz, DMSO-d$_6$): δ 13.37 (s, 1H), 8.61-8.53 (m, 2H), 8.32 (d, J=13.6 Hz, 1H), 8.21 (d, J=9.0 Hz, 1H), 8.16 (d, J=6.0 Hz, 1H), 7.80-7.71 (m, 2H), 7.49 (d, J=8.2 Hz, 1H), 7.42-7.32 (m, 4H), 7.32-7.22 (m, 6H), 6.86 (d, J=5.4 Hz, 1H), 6.46 (d, J=5.0 Hz, 1H), 5.56 (s, 2H), 4.70 (s, 1H), 3.90 (s, 2H), 1.26 (s, 6H).

Example 19

Synthesis of Comparative Compound C

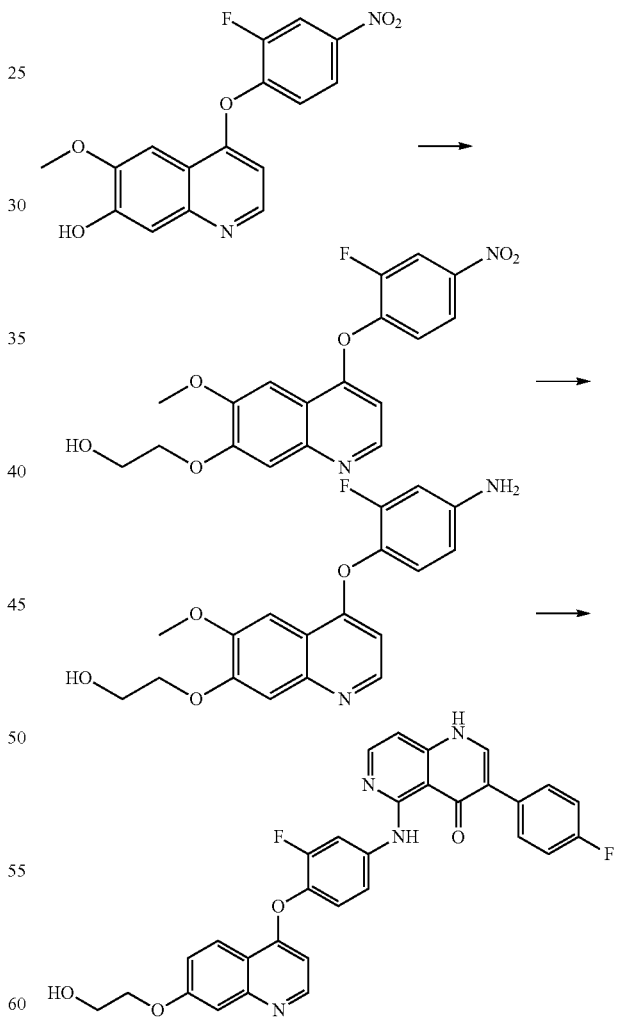

Comparative compound C

In order to further investigate the substituent effect of branched alkyl and linear alkyl side chain at 7-position of quinoline ring on kinase inhibiting activity, comparative compound C were also synthesized. The preparation method was similar to Example 4, except that 2-methyloxirane was replaced with 2-iodoethanol. $^1$H NMR (400 MHz, DMSO-$d_6$): δ 13.33 (s, 1H), 12.91 (s, 1H), 8.83 (d, J=6.4 Hz, 1H), 8.23-8.29 (m, 2H), 8.07 (d, J=6.4 Hz, 1H), 7.69-7.75 (m, 2H), 7.56-7.63 (m, 1H), 7.46 (d, J=8.0 Hz, 2H), 7.25 (t, J=7.2 Hz, 2H), 7.15 (d, J=6.4 Hz, 1H), 7.09 (d, J=8.0 Hz, 2H), 6.98 (d, J=9.0 Hz, 1H), 4.26 (t, J=4.8 Hz, 2H), 3.86 (t, J=4.8 Hz, 2H).

Example 20

Synthesis of Comparative Compound D

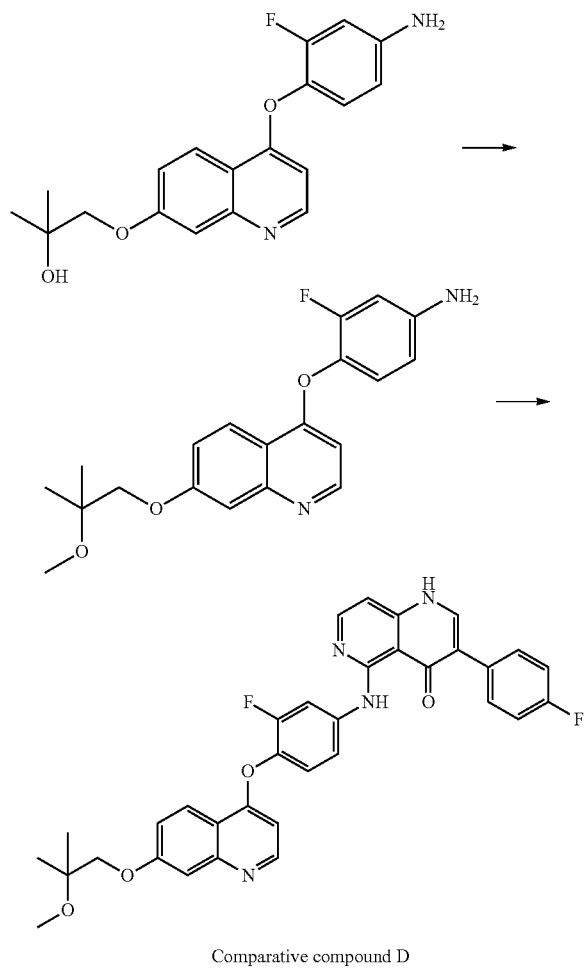

Comparative compound D

In order to further investigate the influence of the hydroxyl group in branched alkyl chain at 7- of quinoline ring on kinase inhibiting activity, comparative compound D were also synthesized.

Step 1: Synthesis of 3-fluoro-4-((7-(2-methoxy-2-methylpropoxy) quinolin-4-yl)oxy) aniline 1-((4-(4-amino-2-fluorophenoxy)quinolin-7-yl)oxy)-2-methylpropan-2-ol (324 mg, 0.84 mmol) and anhydrous potassium carbonate (170 mg, 1.23 mmol) were added into a pear-shaped flask of 25 mL. DMF (10 mL) and iodomethane (310 mg, 2.18 mmol) were added and stirred for 2.5 h. The reactant was poured into water (40 mL). The insoluble material was filtered. The filter cake was washed with water, and dried in vacuum, to obtain pale yellow solid.

Step 2: Synthesis of Comparative Compound D 3-fluoro-4-((7-(2-methoxy-2-methylpropoxy)quinolin-4-yl)oxy)aniline (42 mg, 0.117 mmol) and 5-chloro-3-(4-fluorophenyl)-1,6-naphthyridin-4(1H)-one (33 mg, 0.12 mmol) were added into a pear-shaped flask of 25 mL. Then isopropanol (8 mL) and concentrated hydrochloric acid (1 drop) were added. It was heated to 90° C. and allowed to react for 1 h. The insoluble material was filtered. The filter cake was dissolved in 10 mL mixed solvent of dichlormethane and methanol. Equivalent amount of triethylamine was added. The mixture was stirred at room temperature for 0.5 h. The precipitated solid was filtered and dried to obtain white solid. $^1$H NMR (600 MHz, DMSO-$d_6$): δ 13.34 (s, 1H), 12.86 (s, 1H), 8.84 (d, J=6.4 Hz, 1H), 8.24-8.29 (m, 2H), 8.08 (d, J=6.4 Hz, 1H), 7.67-7.76 (m, 3H), 7.56-7.62 (m, 2H), 7.46 (d, J=8.0 Hz, 1H), 7.26 (t, J=8.8 Hz, 2H), 7.13 (d, J=6.8 Hz, 1H), 7.09 (d, J=8.0 Hz, 1H), 6.97 (d, J=6.0 Hz, 1H), 4.10 (s, 2H), 3.27 (s, 3H), 1.30 (s, 6H).

Example 21

A study on inhibition of protein kinases activity at in vitro biochemical level

Material and method: kinases such as c-Met, VEGFR-2, Axl and RET, obtained from Invitrogen; HTRF KinEASE; TK kit (Cisbio Company); 384-well plate (Greiner Company); ATP (Sigma Company), MgCl$_2$ (Sigma Company); PHERAstar FS multifunctional plate reader (BMG Company); conventional centrifuge (StaiteXiangyi Company); incubator (Binder Company). Typical compounds A and B revealed in patent WO2013097753 are chosen as the Control compounds, and their structures are as following:

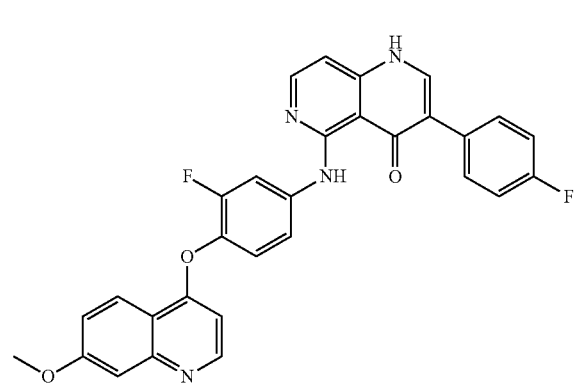

Typical compound A/Example 7
(WO2013097753)

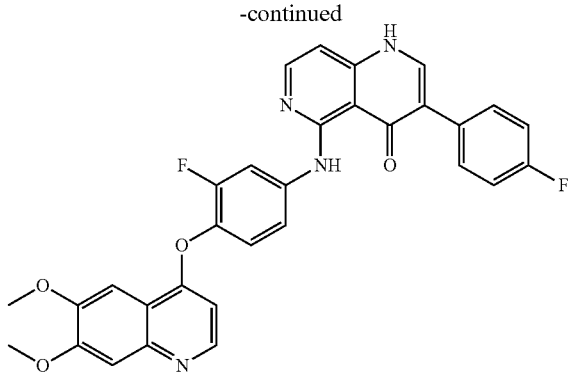

Typical compound B/Example 19
(WO2013097753)

Dilution and storage of compounds: depending on solubility, the test compounds are prepared as stock solutions of 0.5-10 mmol/L with dimethyl sulphoxide (DMSO), and aliquots of the stock are stored at −20° C.;

Preparation of working solution of the compounds: Before test, aliquots of the compounds are removed from the refrigerator, and diluted with pure DMSO to 50× of the level needed; and then the compounds are diluted with deionized water to 4× of the level needed;

Preparation of 1.33× enzymatic buffer: 5× enzymatic buffer (from HTRF kit) is diluted to 1.33× with deionized water, and appropriate components of the final level 1.33× are added: 1.33 mmol/L dithiothreitol (DTT) and 1.33 mmol/L MgCl2;

Preparation of kinase working solution: Met is diluted to 2× final level required, 0.2 ng/μL, with 1.33× enzymatic buffer;

Preparation of substrate working solution: the substrate labeled with biotin (from HTRF kit) and ATP (10 mM) are diluted with 1.33× enzymatic buffer to prepare a mixture at 4× of the final level required;

Preparation of the testing working solution: Streptavidin-XL665, 16.67 μmol/L is diluted with HTRF test buffer to 4× of the final level required, and then mixed with antibody-Cryptate of the same volume (both from the HTRF kit).

Enzymatic reaction step: 4 μl of kinase working solution is added to each well of the low volume 384-well plate. Meanwhile, 4 μL 1.33× enzymatic buffer is added as the negative control. 2 μL compound working solution is added into each well, and 2 μL 8% DMSO in water is added as zero compound level control (i.e., positive control). At 25° C. (or 30 C), incubate for 5-10 min; add 2 μL substrate working solution into each well to initiate the enzymatic reaction. Allow to react while shaking at 25° C. (or 30° C.) for 15-60 min.

HTRF reagent testing step: 8 μL testing working solution is added into each well to terminate the reaction; allow to react at 25° C. for 1 h;

Reading HTRF signal: PHERAstar FS is used to read the testing signal, and its setting is as following:

Optic module HTRF®
Integration delay (lag time) 50 μs
Integration time 400 μs
Number of flashes 200
For the original data read from each well, ratio=665 nm/620 nm;

Estimation of inhibition rate:

$$\text{Inhibition ratio} = \left(1 - \frac{\text{Test ratio} - \text{Negative control ratio}}{\text{Positive control ratio} - \text{negative control ratio}}\right) \times 100$$

Estimation $IC_{50}$: The log of compound level serves as the X-axis, and the inhibition rate as the Y-axis. In GraphPad Prism 5, a non-linear curve is fitted: log (inhibitor) vs. response—Variable slope. $IC_{50}$ is obtained by estimating the test compound level when the enzymatic activity inhibition rate is 50%.

Study results: 50% inhibition level ($IC_{50}$, nM) of activity of c-Met, VEGFR-2, Axl and RET kinase See Table 1 for the 50% inhibition level ($IC_{50}$) of compounds provided by this invention and with a structure indicated by Formula I for c-Met and VEGFR-2:

TABLE 1

Inhibition of the compounds on kinases c-Met and VEGFR-2

| Example No. | $IC_{50}$ (nM) | |
| --- | --- | --- |
| | c-Met (h) | VEGFR-2 (h) |
| Example 1 | 19.4 | 47.1 |
| Example 2 | 15.6 | 28.4 |
| Example 3 | 20.1 | 48.9 |
| Example 4 | 2.07 | 0.39 |
| Example 5 | 9.4 | 29.5 |
| Example 6 | 7.9 | 31.2 |
| Example 7 | 7.4 | 10.2 |
| Example 8 | 16.8 | 36.4 |
| Example 9 | 13.3 | 28.0 |
| Example 10 | 12.7 | >5000 |
| Example 11 | 9.5 | >5000 |
| Example 12 | 7.2 | >5000 |
| Example 13 | 9.0 | >5000 |
| Example 14 | 14.3 | >5000 |
| Example 15 | 22.4 | >5000 |
| Example 16 | 14.4 | >5000 |
| Example 17 | 40.0 | >5000 |
| Example 18 | 40.3 | >5000 |
| Comparative compound A | 68.3 | 124.9 |
| Comparative compound B | 142.7 | 181.6 |
| Comparative compound C | 5.7 | 8.5 |
| Comparative compound D | 12.1 | 60.0 |

Further test shows that, Example 4 and Example 7 demonstrate good inhibition on Axl kinase, with $IC_{50}$ being 15.7 and 14.9 nM, respectively; as well as good inhibition on RET, with $IC_{50}$ being 62.0 and 53.0 nM, respectively.

Example 21

An In Vivo Pharmacokinetic Study in Rats

For comparison, Example 4 and comparative compound C are given to rats in the form of polyglycol 400 in water (70%). For intravenous injection, rats are given a dose of 1 mg/kg. For oral administration, rats are given a dose of 5 mg/kg. 15, 30, 45 min, 1, 2, 4, 6, 8, 10 and 24 h after Example 4 and comparative compound C are given orally, around 0.3 mL of blood sample is collected into a heparinized Eppendorf tube from each rat. 5, 15, 30 min, 1, 2, 4, 6, 8, 10 and 24 h after introvenous injection of Example 4 and comparative compound C, around 0.3 mL of blood sample is collected into a heparinized Eppendorf tube from each rat, and stored on dry ice temporarily until centrifuge. The whole blood is centrifuged at 8000 rpm for 5 min to collect plasma, which is then transferred to 96-well pallet, and stored at −20° C. till LC-MS/MS testing.

Pharmacokinetic parameters among rats after medication are estimated using the non-compartment model of software WinNonlin.

The peak concentration, Cmax: the actual measurements are used;

The area under the concentration-time curve, AUC0-t: it is estimated using trapezoidal rule; $AUC_{0-\infty}=AUC_{0-t}+Ct/ke$, Ct is the plasma concentration of the last detachable time point, and ke is the elimination rate constant;

Elimination half-life, $t_{1/2}$=0.693/$ke$;

Absolute bioavailability, $F$=Dose$_{iv}$*$AUC_{0-t,ig}$/Dose$_{ig}$*$AUC_{0-t,iv}$×100%.

Table 2 listed the pharmacokinetic parameters of Example 4 and comparative compound C in rats after intravenous injection or oral administration. The results show that, Example 4 has good pharmacokinetic nature, including ideal clearance rate (CL), half-life ($t_{1/2}$) and exposure dose ($AUC_{0-t}$). Under the same dose, oral exposure dose of Example 4 is 22 times of that of comparative compound C, and also has significantly higher bioavailability of comparative compound C.

TABLE 2

Pharmacokinetic data of Example 4 and Comparative compound C in rats

| N.O. | Example 4 | | Comparative compound C | |
|---|---|---|---|---|
| | 1 mg/kg (i.v.) | 5 mg/kg (i.g.) | 1 mg/kg (i.v.) | 5 mg/kg (i.g.) |
| $t_{1/2}$ (h) | 9.97 | 8.37 | 2.35 | 2.14 |
| $C_{max}$ (μg/mL) | 10.85 | 4.31 | 0.97 | 0.53 |
| $AUC_{0-t}$ (h * μg/mL) | 11.5 | 41.28 | 2.29 | 1.85 |
| Vz (L/kg) | 0.47 | 1.46 | 1.21 | 7.89 |
| CL (L/h/kg) | 0.03 | 0.12 | 0.29 | 1.90 |
| F (%) | — | 71.8 | — | 16.2 |

Example 22

Tumor Xenograft Model

Efficacy of the compounds of this invention is evaluated through standard murine model of transplanted tumor. Human tumor cells (U87MG neurospongioma cell, MKN45 gastric adenocarcinoma cell, Caki-1 renal carcinoma cell, HUH 7 hepatoma cell, NCI-H441 epithelial cell of lung adenocarcinoma, MDA-MB-231 breast cancer cell, SMMC-7721 hepatoma cell, ATCC) are cultured and collected, and then female nude mice (BALB/cA nu/nu, Shanghai Laboratory Animal Center (SLAC)) at an age of 6-7 weeks are inoculated subcutaneously at posterior abdomen. When the size of the tumor reaches 150 mm$^3$, animals are randomized into the solvent control group (70% PEG-400 in water) and the compound group (6 animals per each group). Subsequently, the compound is given to the animals through lavage (3-10 mpk/dose, dissolved in 70% PEG-400 in water), starting from any time between 0 to 22 days after inoculation of tumor cells, and usually once every day during the study.

Tumor Growth Inhibition (TGI) Analysis

Development and growth of tumor is evaluated through the relationship between tumor size and time. The long axis (L) and short axis (W) of the subcutaneous tumor are measured twice every week with a caliper, and the tumor volume (TV) is calculated with equation (L×W2)/2). TGI is estimated as the difference between the median tumor size of mice in the solvent group and drug group, expressed as percentage of the median tumor size of mice in the solvent control group, and calculated with the equation as following:

$$\% \ TGI = \left( \frac{\text{Median tumor volume(control)} - \text{Median tumor volume(medication)}}{\text{Median tumor volume(control)}} \right) \times 100$$

Partially resolved (PR) tumor: when the tumor size at the last medication is smaller than the tumor size at the initial medication, it is considered as resolved tumor.

The original statistical analysis is done through repeated measures ANOVA (RMANOVA). Subsequently, multiple comparisons are carried out though Scheffe psot hoc test. Solvent alone (70% PEG-400 and so on) is the negative control.

FIG. 1 illustrates inhibiting effect of Example 4 on tumor growth in U87MG glioblastoma model. Example 4 is given orally (p.o.) at a dose of 3 and 10 mg/kg everyday (QD) for 22 days. All doses have statistical significance, and could inhibit growth of U87MG tumor under the skin of nude mouse in a dose dependent manner. On the last day of medication (day 22), the mean tumor size is compared with that of the solvent group, and the doses of 3 and 10 mg/kg show tumor growth inhibition (TGI) of 87.0% and 105.9% of the mean tumor size, respectively.

TABLE 3

Tumor inhibition in U87MG model

| | Tumor growth inhibition rate, % TGI | | |
|---|---|---|---|
| Compound No. | 3 mg/kg | 10 mg/kg | Regression of tumor |
| Example 4 | 87.0 | 105.9 | Tumor regression rate is 100% (6/6) |
| Comparative compound A | — | 55.3 | No tumor regression is noted (0/6) |

The preferable embodiments of this inventions has been detailed above, however, this invention is not limited to details in the embodiments described above. Various simple revisions may be applied to the technological scheme of this invention within the technological principle, and all such simple revisions are also protected by this invention.

It should also be noted that, all specific technical characteristics described in the embodiments above may be combined in any proper way as long as no conflict will be caused. In order to avoid any unnecessary repetition, this invention will not describe possible combinations.

Moreover, different embodiments of this invention may also be combined freely, as long as it is not against the principle of this invention, and such combinations should also be treated as content that this invention reveals.

What is claimed is:

1. A naphthyridine compound as shown by Formula (I), or its stereoisomers, geometric isomers, tautomers, nitrogen oxides, hydrates, solvates, metabolites, pharmaceutically acceptable salts or their prodrugs:

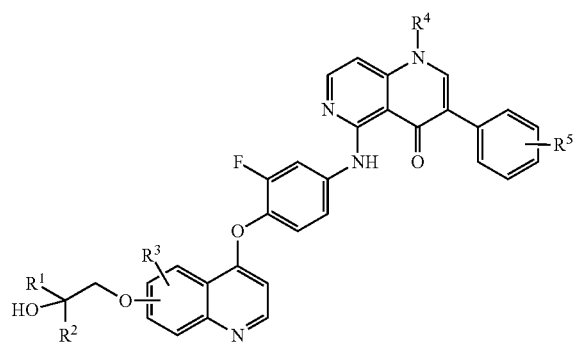

(I)

wherein:
- $R^1$ and $R^2$ are chosen from H and $C_1$-$C_3$ alkyl, and $R^1$ and $R^2$ may not be hydrogen simultaneously;
- $R^3$ is chosen from H and $C_1$-$C_3$ alkoxyl;
- $R^4$ is chosen from hydrogen, methyl, ethyl, propyl, isopropyl, cyclopropyl,

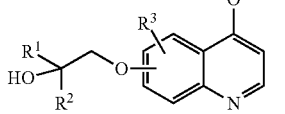

2-methoxyethyl, 2-hydroxyethyl or benzyl;
- $R^5$ is chosen from H, F, Cl, Br, I, CN, $C_{1-3}$ alkyl, or $C_{1-3}$ haloalkyl, and and $R^3$ are located at 6- and 7- of the quinolyl ring, or 7- and 6- of the quinolyl ring, respectively.

2. The compound according to claim 1, wherein, the naphthyridine compound has one of the following structures:

(6)
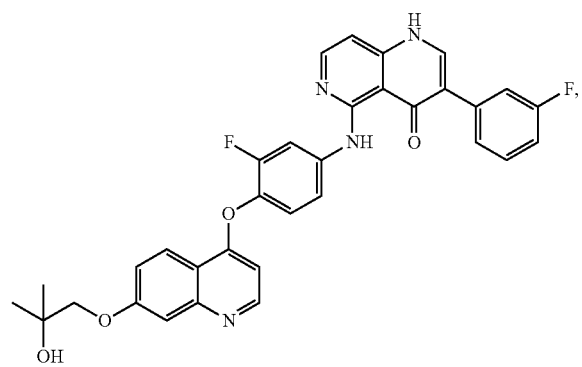
(7)
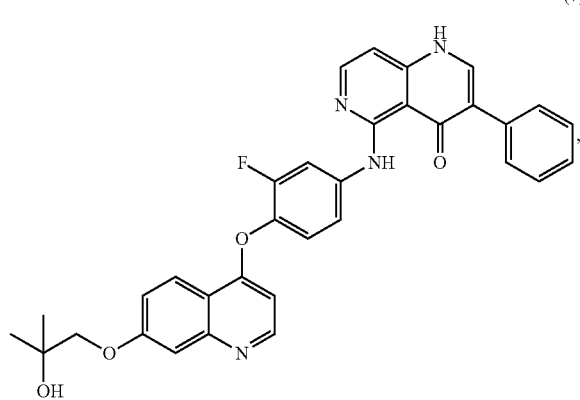
(8)
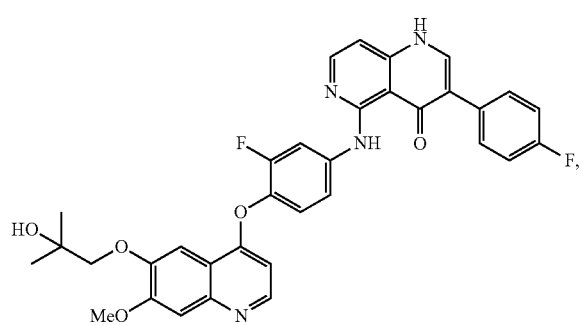
(9)
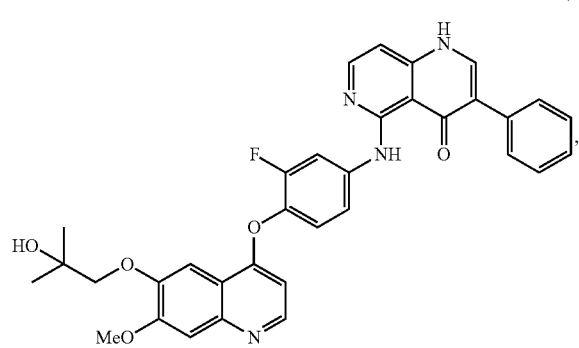
(10)
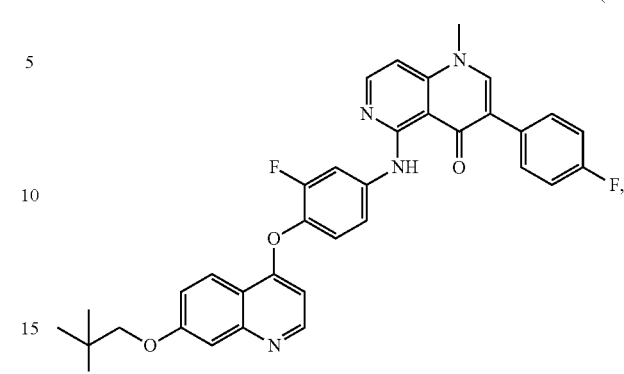
(11)
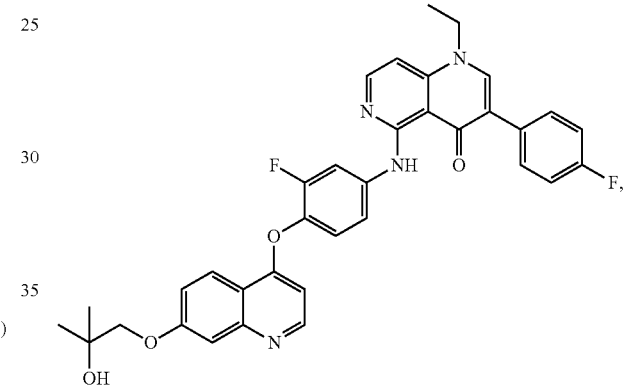
(12)
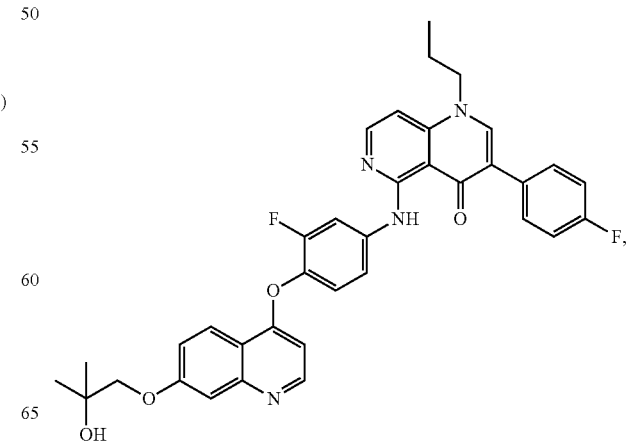

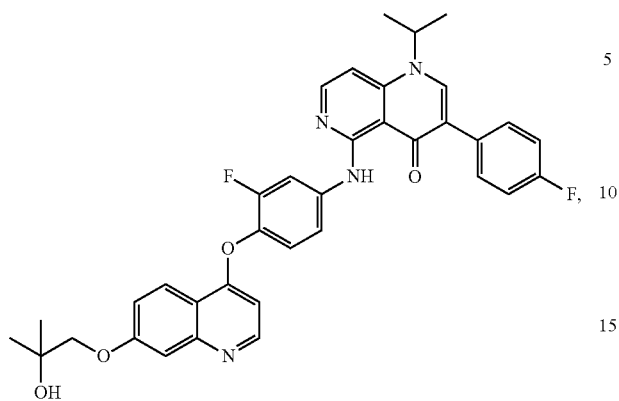

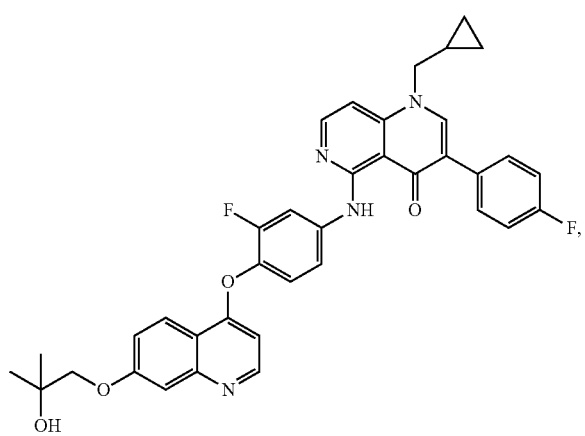

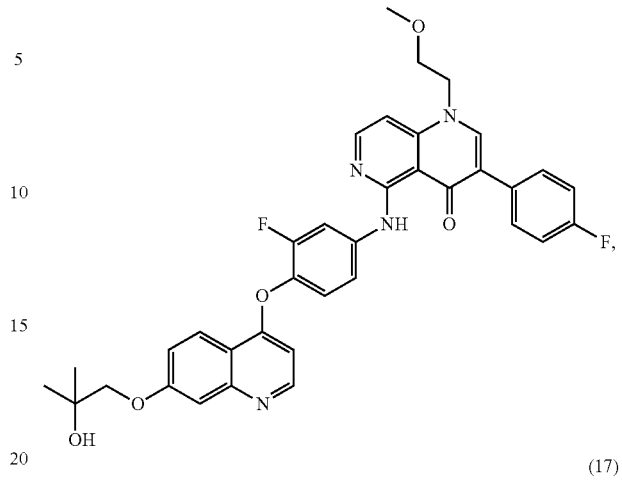

or their stereoisomers, geometric isomers, tautomers, nitrogen oxides, hydrates, solvates, metabolites, pharmaceutically acceptable salts or their prodrugs.

3. A medical combination, which includes a pharmaceutically acceptable carrier, vehicle or diluent, and a compound defined in claim 1 serving as active ingredient.

4. A method of modulating c-Met, VEGFR-2, Axl, or RET by administering a compound according to claim 1 to a patient in need thereof.

5. A method of treating disease selected from colorectal carcinoma, carcinoma of urinary bladder, breast cancer, hepatoma, lung cancer, pancreatic cancer, gastrointestinal cancer, leukemia, ovarian cancer, head-and-neck cancer, prostatic carcinoma, renal carcinoma, nasopharyngeal carcinoma, spongioblastoma, squamous carcinoma, astrocytoma, Kaposi's sarcoma, melanoma, neuroglioma, urogenital cancer, myeloproliferative diseases, atherosclerosis or pulmonary fibrosis by administering a compound according to claim 1 to a patient in need thereof.

* * * * *